(12) United States Patent
Vossmeyer et al.

(10) Patent No.: US 7,211,439 B2
(45) Date of Patent: May 1, 2007

(54) SELECTIVE CHEMICAL SENSORS BASED ON INTERLINKED NANOPARTICLE ASSEMBLIES

(75) Inventors: Tobias Vossmeyer, Fellbach (DE); Isabelle Besnard, Tuebingen (DE); Jurina Wessels, Stuttgart (DE); William E. Ford, Stuttgart (DE); Akio Yasuda, Stuttgart (DE)

(73) Assignee: Sony Deutschland GmbH, Cologne (DE)

( * ) Notice: Subject to any disclaimer, the term of this patent is extended or adjusted under 35 U.S.C. 154(b) by 332 days.

(21) Appl. No.: 10/013,388

(22) Filed: Dec. 11, 2001

(65) Prior Publication Data
US 2002/0132361 A1   Sep. 19, 2002

(30) Foreign Application Priority Data
Dec. 12, 2000   (EP) .................................. 00127149

(51) Int. Cl.
*G01N 30/00* (2006.01)
(52) U.S. Cl. .......................... 436/151; 422/50; 422/55; 422/56; 422/68.1
(58) Field of Classification Search ............. 422/50, 422/55, 61, 68.1, 82.01, 82.05, 83, 88; 436/73, 436/74, 149, 164
See application file for complete search history.

(56) References Cited

FOREIGN PATENT DOCUMENTS

| | | |
|---|---|---|
| EP | 1 022 560 | 7/2000 |
| FR | 2783051 | 3/2000 |
| WO | WO 96/07487 | 3/1996 |
| WO | WO 99/27357 | 6/1999 |
| WO | WO 99/40423 | 8/1999 |
| WO | WO 99/67627 | 12/1999 |
| WO | WO 00/00808 | 1/2000 |

OTHER PUBLICATIONS

"Array-Based Vapor Sensing Using Chemically Sensitive, Carbon Black-Polymer Resistors", Chem Mater 1996, 8, M.C. Lonergan et al., pp. 2298-2312.
"Quantitative Study of the Resolving Power of Arrays of Carbon Black-Polymer Composites in Various Vapor-Sensing Tasks", Anal. Chem. 1998, 70, B.J. Doleman et al., pp. 4177-4190.
"Highly Sensitive Detection and Discrimination of Biogenic Amines Utilizing Arrays of Polyaniline/Carbon Black Composite Vapor Detectors" Chem. Mater. 2000, 12, G.A. Sotzing et al., pp. 593-595.
Vapour Sensing Using Hybrid Organic-Inorganic Nanostructured Materials, J. Mater. Chem., 2000, 10, S.D. Evans et al., pp. 183-188.

(Continued)

*Primary Examiner*—Jill Warden
*Assistant Examiner*—Samuel P. Siefke
(74) *Attorney, Agent, or Firm*—Oblon, Spivak, McClelland, Maier & Neustadt, P.C.

(57) ABSTRACT

The invention relates to a nanoparticle film comprising a nanoparticle network formed of nanoparticles interlinked by linker molecules. The linker molecules have at least two linker units that can bind to the surface of the nanoparticles. By introducing selectivity-enhancing units in the linker molecule, the selectivity of the nanoparticle film towards target analytes can be enhanced. A fine-tuning of the selectivity can be achieved by including a fine-tuning unit in the vicinity of the selectivity-enhancing unit. The nanoparticle film can be used to produce chemical sensors which are selective and stable in their performance.

20 Claims, 15 Drawing Sheets

OTHER PUBLICATIONS

"Collodial Metal-Insulator-Metal Ensemble Chemiresistor Sensor", Anal. Chem., 1998, 70, H. Wohltjen and A.W. Snow, pp. 2856-2859.

"Effect of Interchain Hydrogen Bonding on Electron Transfer Through Alkanethiol Monolayers Containing Amide Bonds", J. Phys. Chem., B 2000, 104, Sek et al., pp. 5399-5402.

"Structures and Properties of Nanopractice Thin Films Formed via a One-Step Exchange-Cross-Linking-Precipitation Route", Anal. Chem., 8 1999, 71, Leibowitz et al., pp. 5076-5083.

"Synthesis and Characterization of Hydrophobic, Organically-Soluble Gold Nanocrystals Functionalized With Primary Amines", Langmuir, 1996, 12, D.V. Leff, L. Brandt, J.R. Heath, p. 4723.

"Synthesis of Thiol-Derivatised Gold Nanoparticles in a Two-Phase Liquid-Liquid System", J. Chem. Soc., Chem. Commun., 1994, Brust and Coworkers, pp. 801-802.

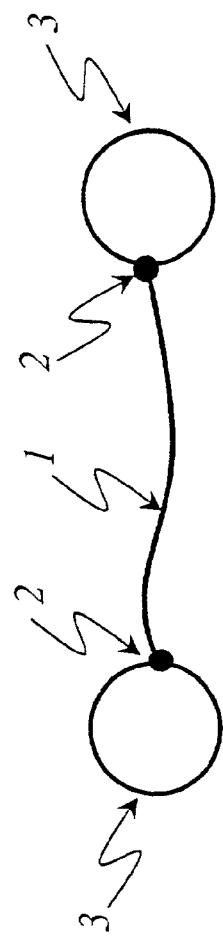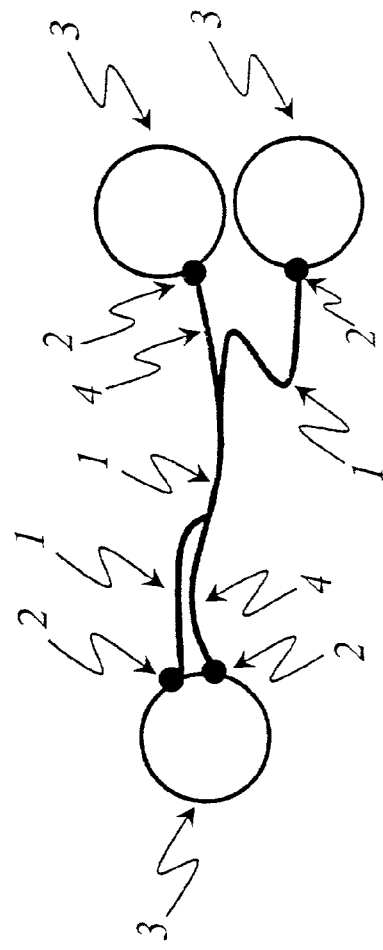
Fig. 1

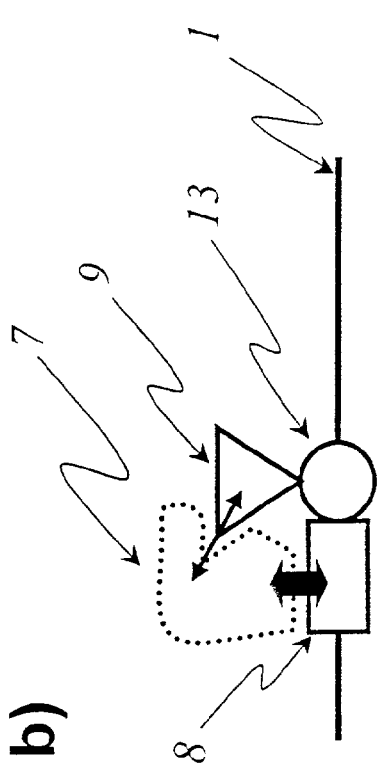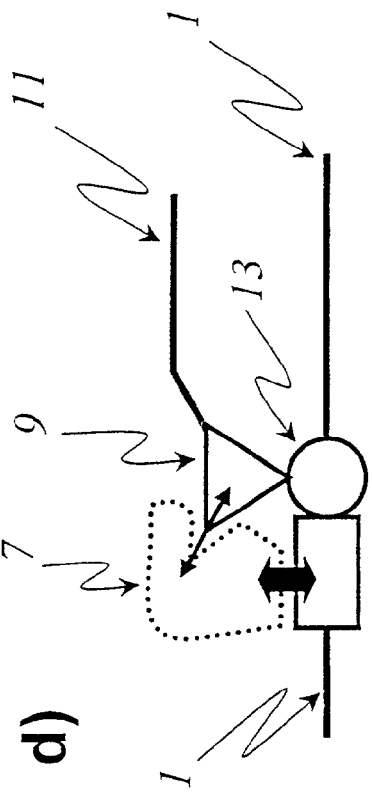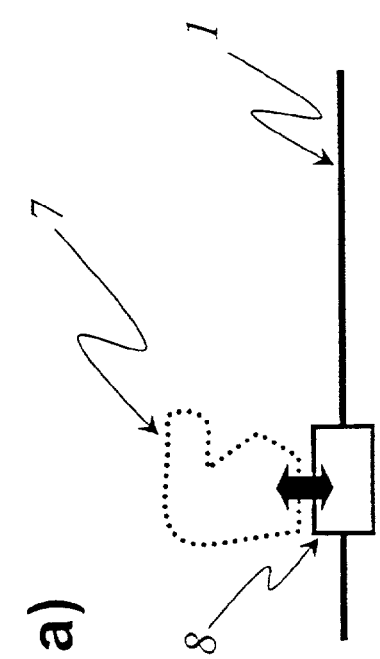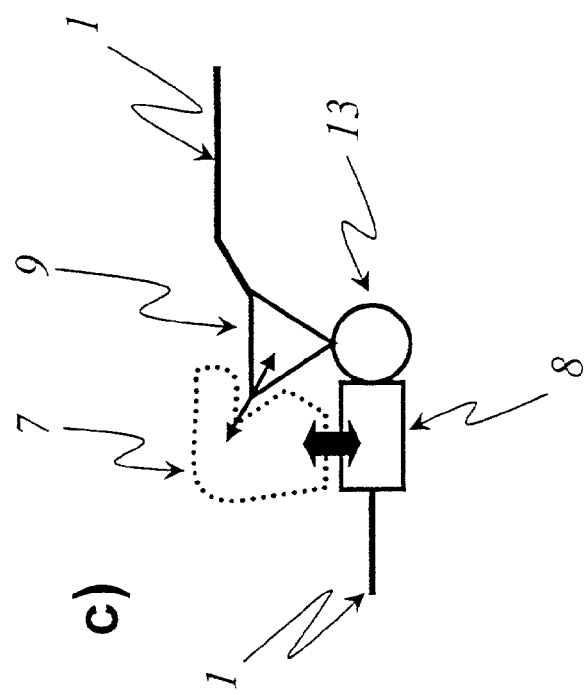
Fig. 2

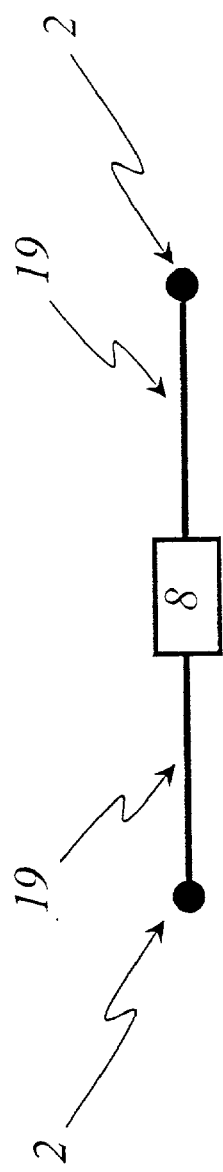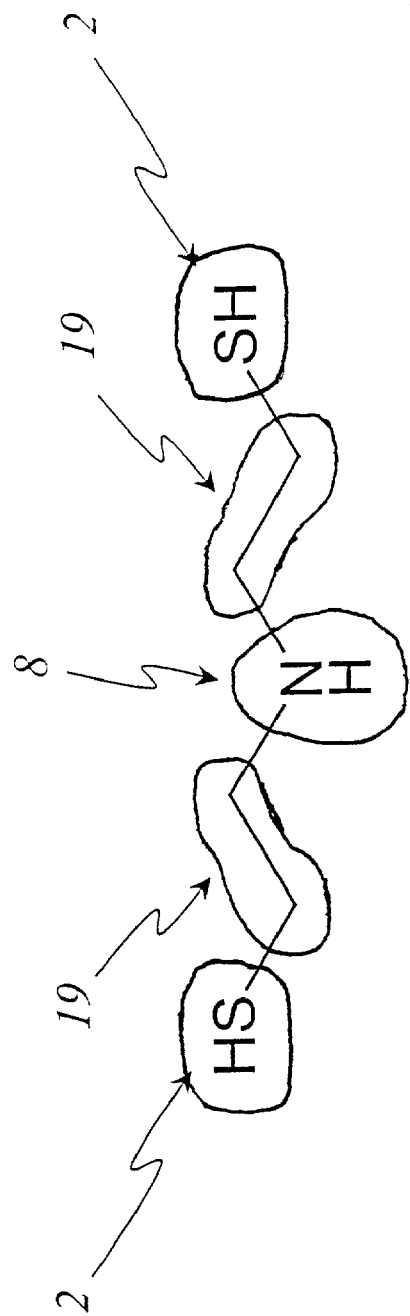
Fig. 3 a)-b)

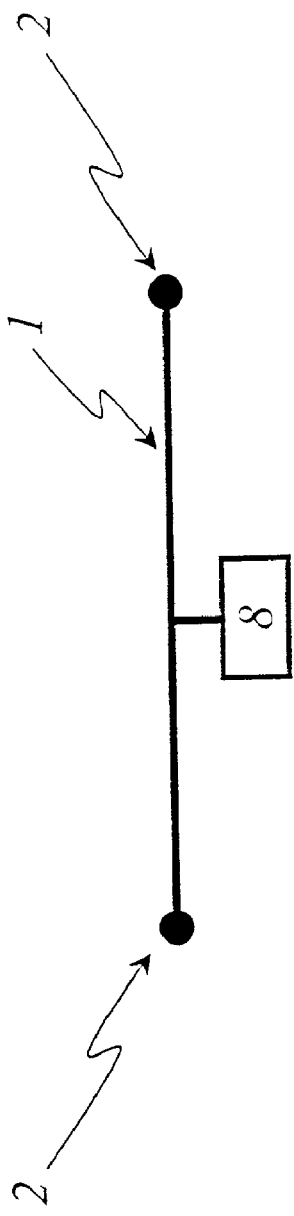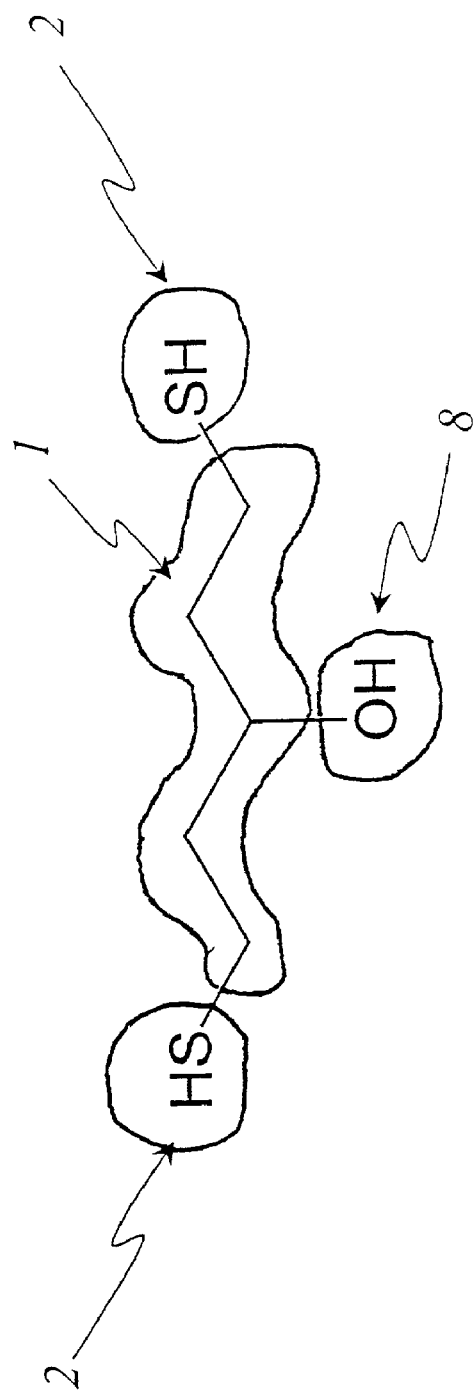
Fig. 3 c)-d)

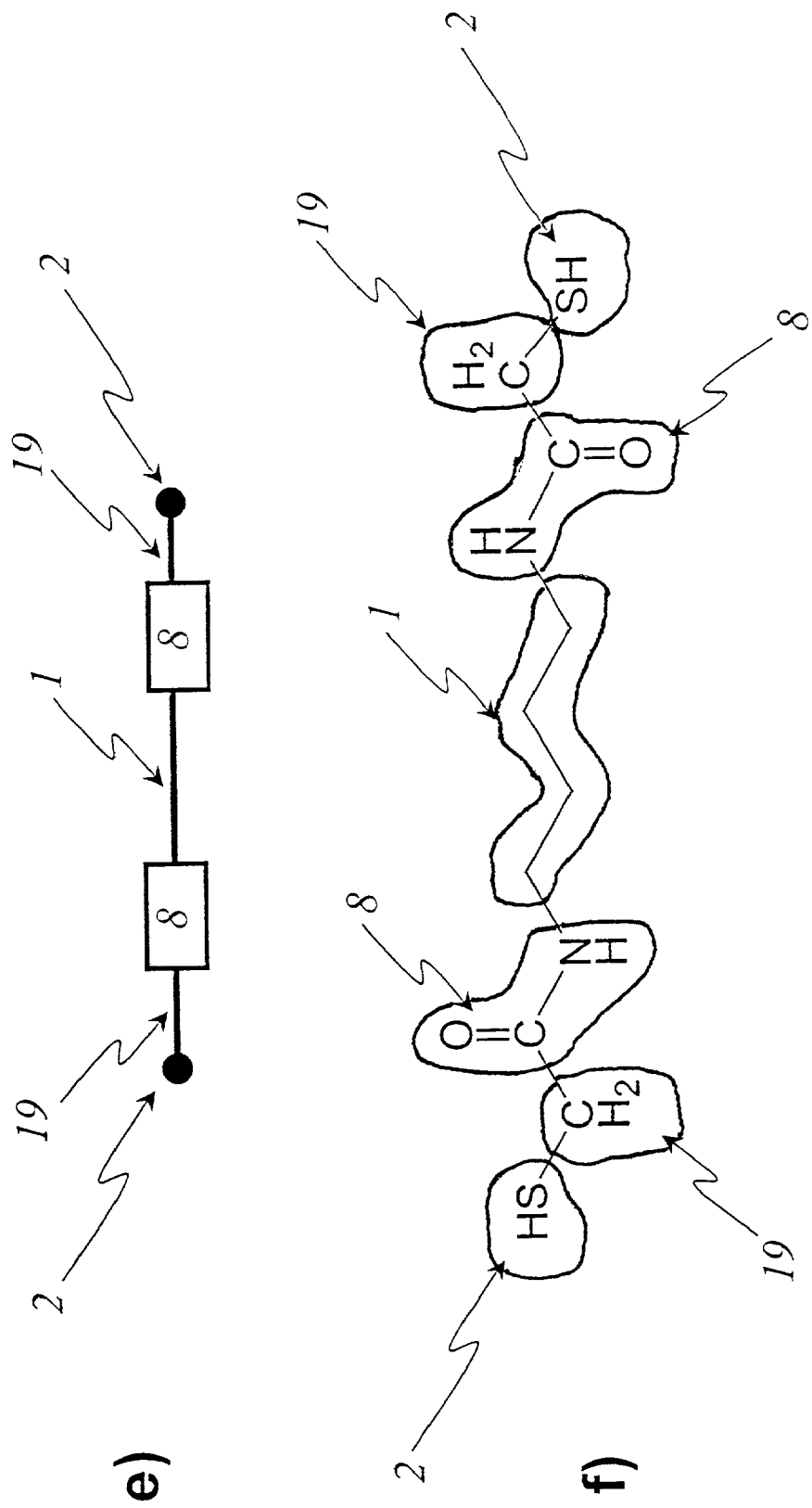
Fig. 3 e)-f)

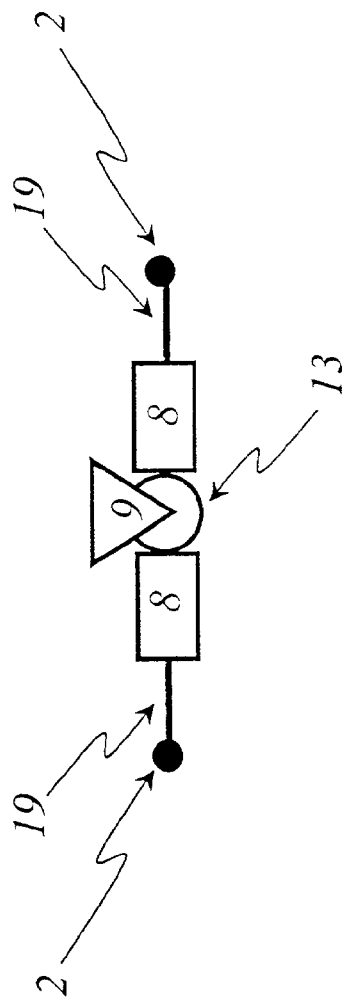
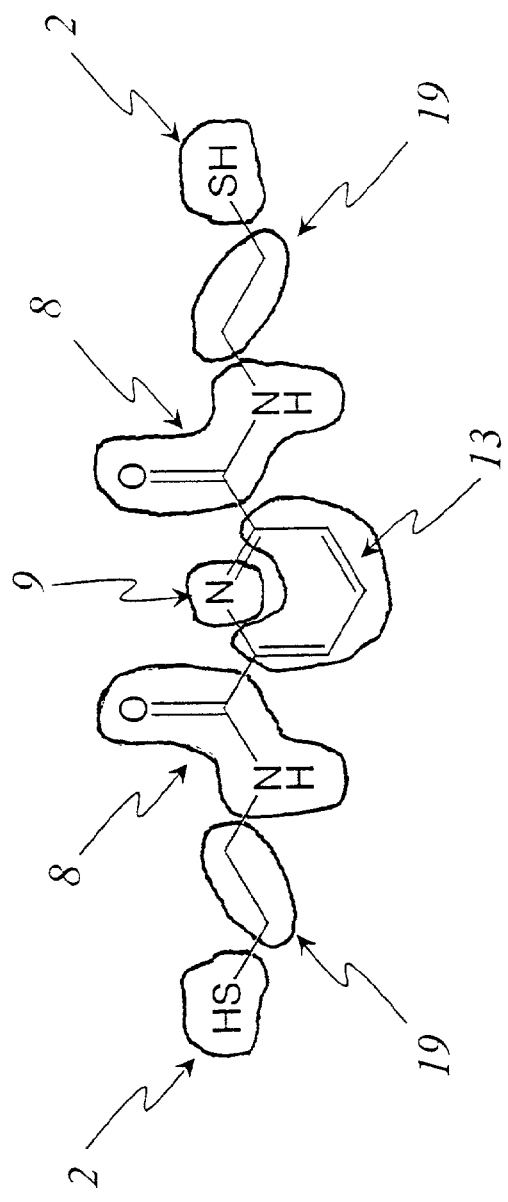
Fig. 3 g)-h)

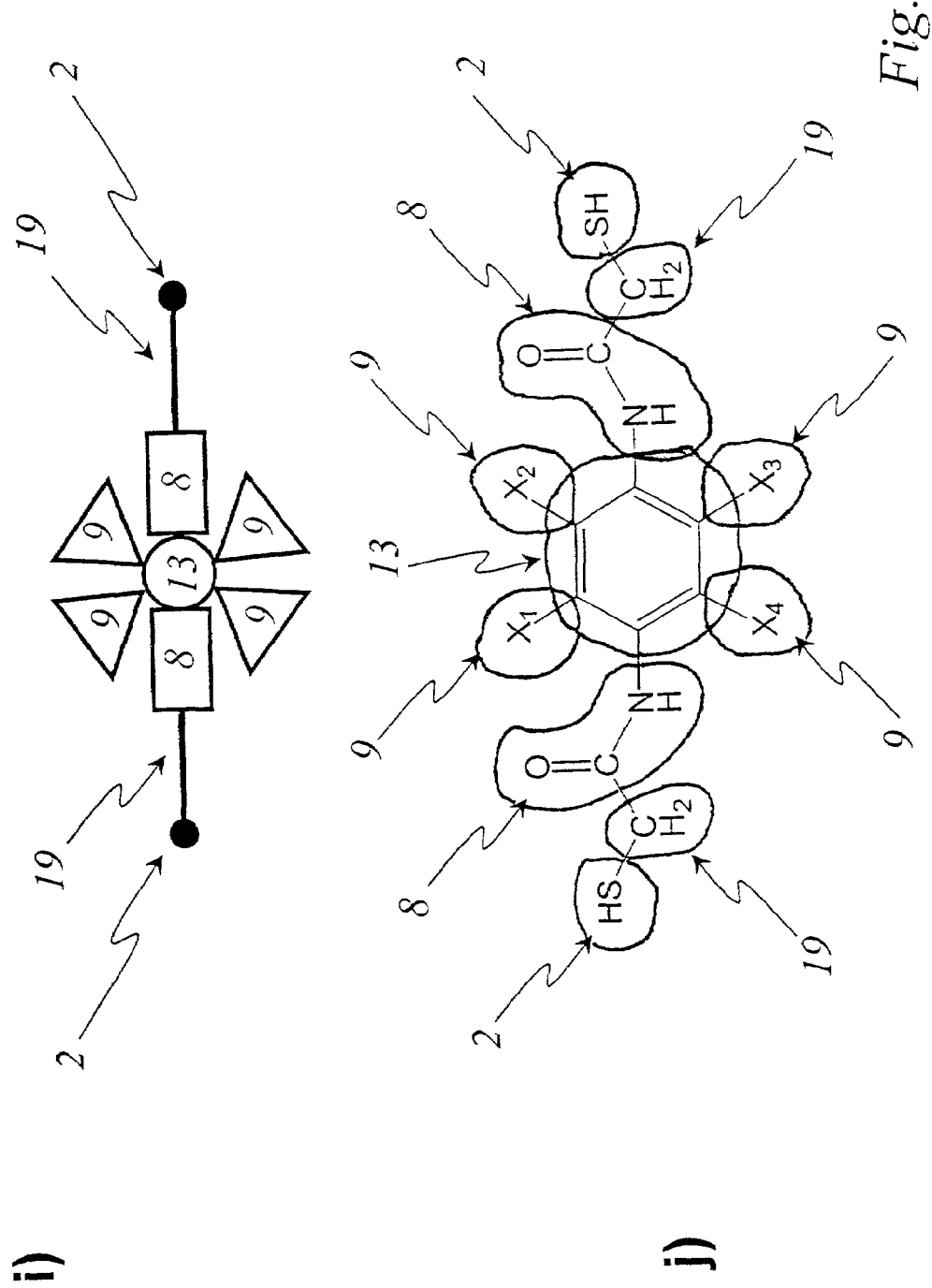
Fig. 3 i)-j)

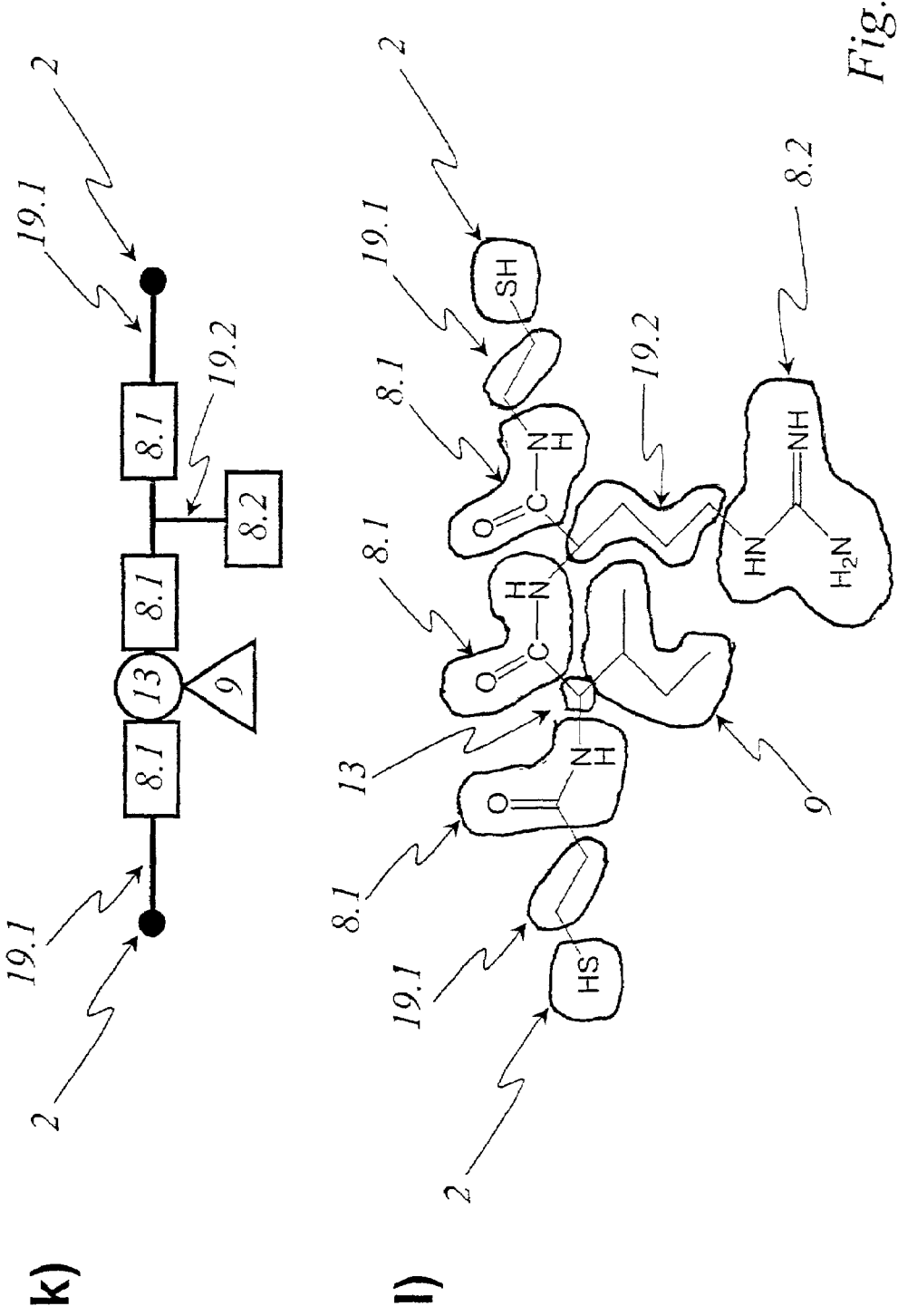
Fig. 3 k)-l)

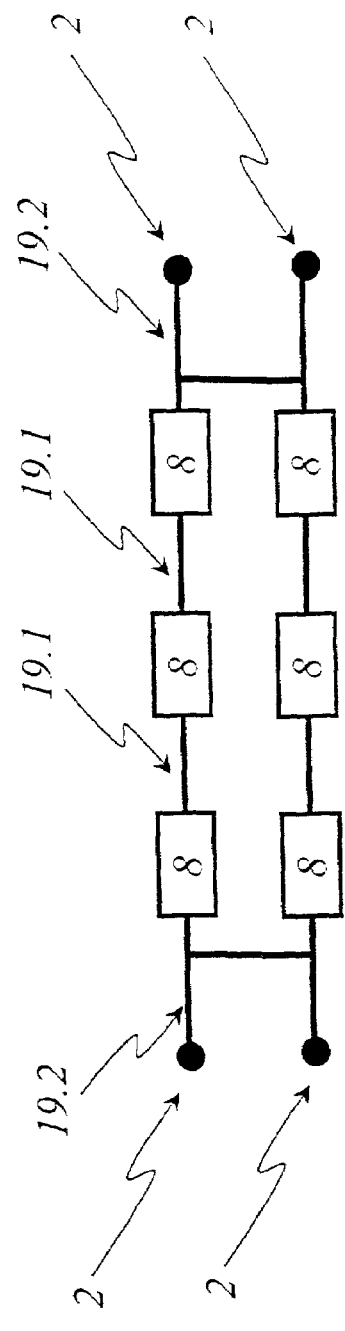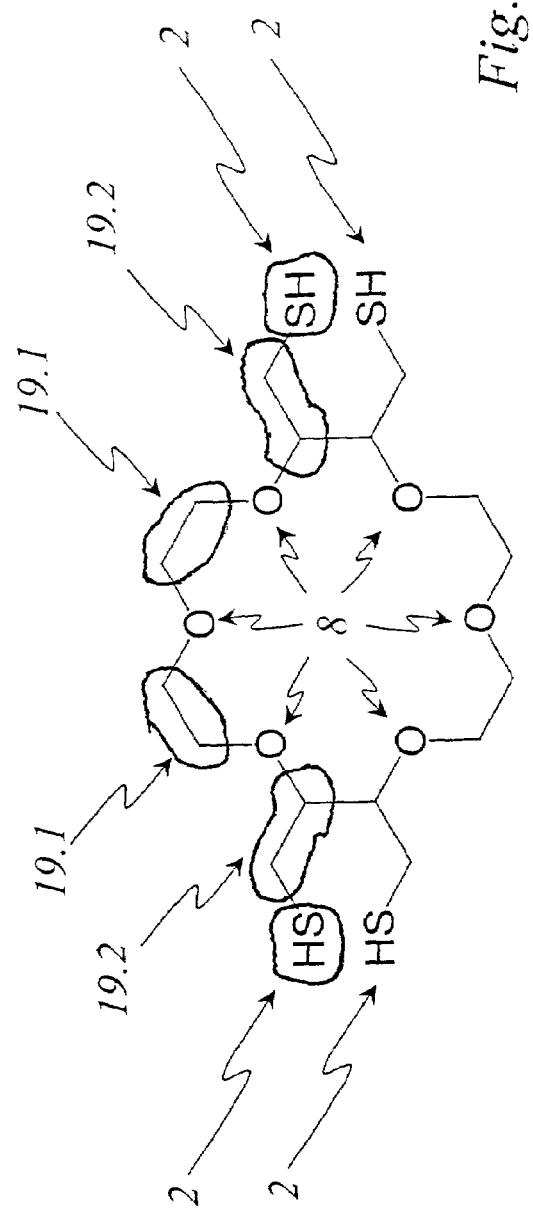
Fig. 3 m)-n)

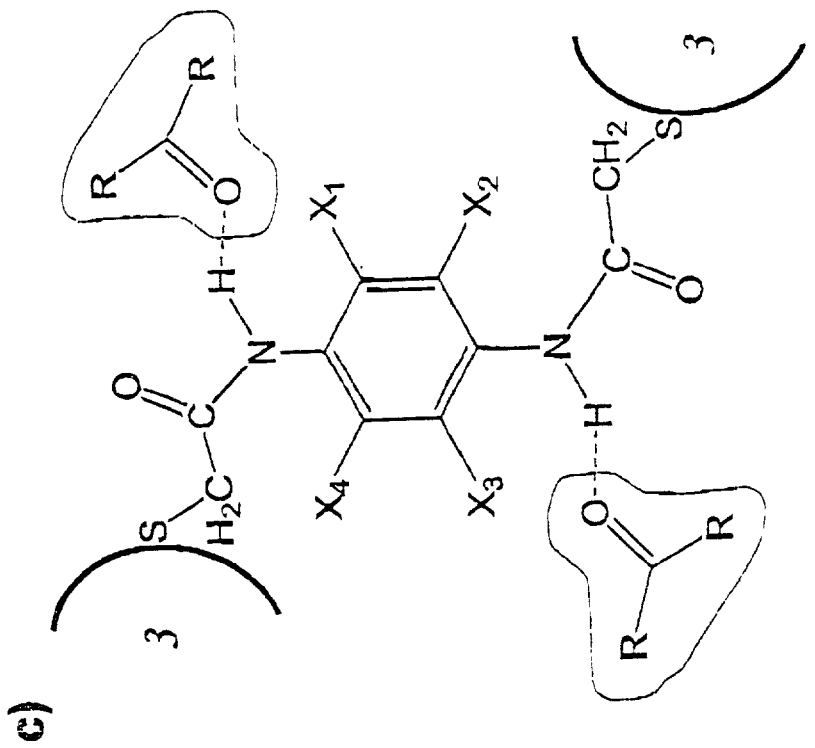
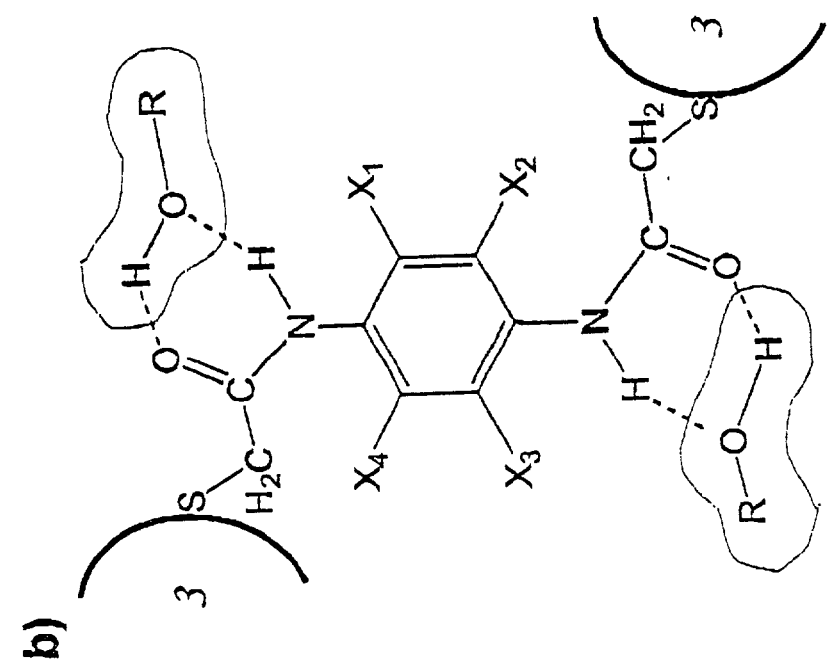
Fig. 4 b)-c)

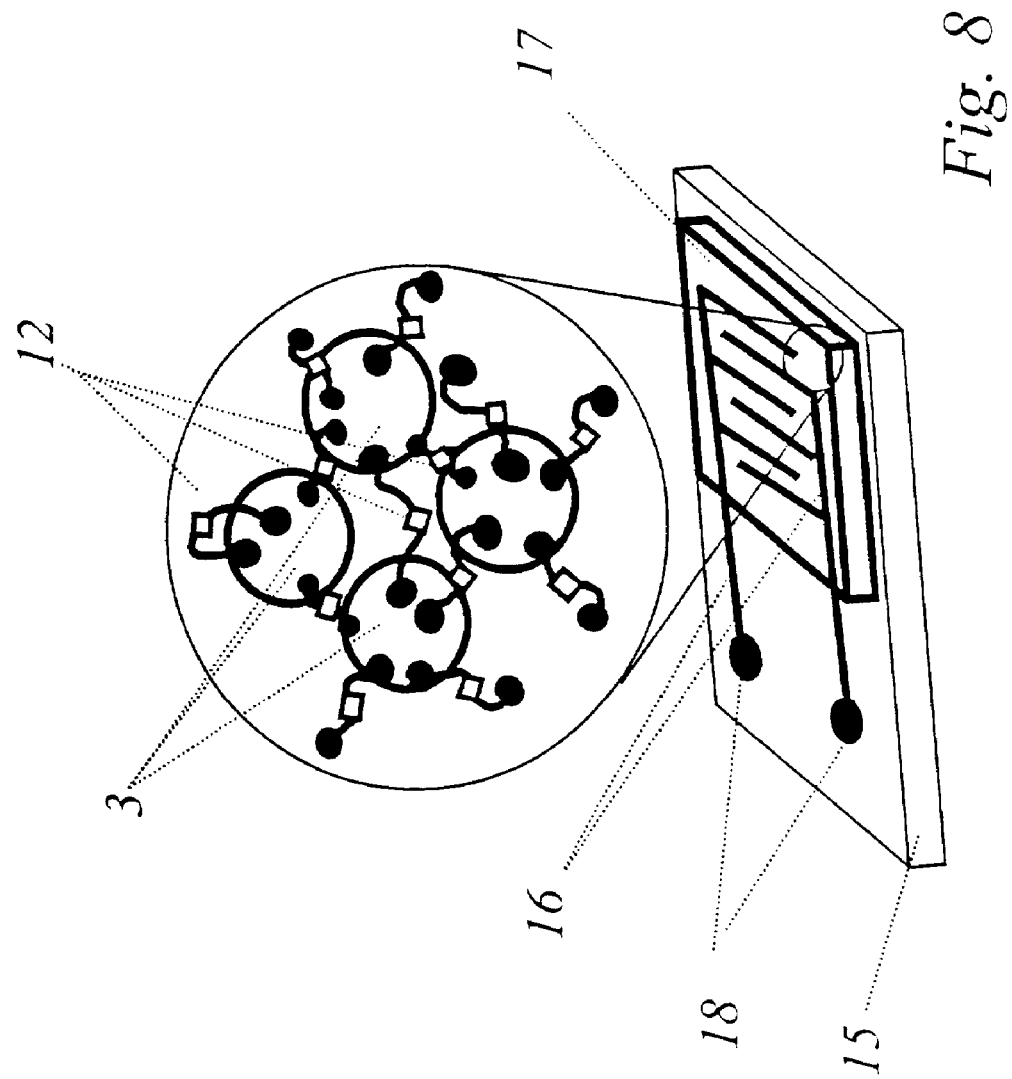

SELECTIVE CHEMICAL SENSORS BASED ON INTERLINKED NANOPARTICLE ASSEMBLIES

The invention relates to a chemical sensor comprising a nanoparticle film, a method for forming such a chemical sensor and a method for detecting an analyte by using said chemical sensor.

Increasing concerns over pollutants within the environment require improved monitoring and/or analysis for the detection of certain chemical species. While analytical techniques are available to detect the presence of many substances down to levels as low as parts per billion or less, such analytical techniques generally require collecting a sample in the field, taking the sample to a laboratory, and analyzing the sample by, e.g. gas chromatography or mass spectroscopy. Such analysis requires sophisticated equipment that generally requires up to several days to obtain final results. Thus, present analytical techniques fail to provide any real-time information about the presence of pollutants or contaminants. To overcome the limitations of such analytical techniques, research has been directed to developing chemical sensors that give more rapid feedback information. Further applications in which a real time monitoring of analytes is required are quality control, e.g. in the production of food, or in medical care.

Recently, a new type of sensor has been developed that is based on electrically conducting nanometer-size particles, each coated by an organic material. The electrically conducting nanoparticles are therefore separated by a thin layer of insulating material. The electrical resistance of such a nanoparticle film can be changed by the presence of a chemical species. Such a film therefore can be used as a chemiresistor by depositing such a nanoparticle film onto a pair of contacting electrodes.

M. C. Lonergan et al., Chem. Mater., 1996, 8, 2298–2312, describe chemically sensitive carbon black polymer resistors. Carbon black-organic polymer composites swell reversibly upon exposure to vapors. To obtain a sensor, thin films of carbon black-organic polymer composites were deposited across two metallic leads. Swelling of the film by the absorption of vapors induced a change in resistance of the films and signaled the presence of an analyte. To identify and classify vapors, arrays of such vapor-sensing elements were constructed, with each element containing the same carbon black conducting phase, but a different organic polymer as the insulating phase The different gas-solid partition coefficients for the various polymers of the sensor array produced a pattern of resistance changes that can be used to classify vapors and vapor mixtures. This type of sensor array can resolve common organic solvents, including molecules of different classes such as aromatics from alcohols, as well as those within a particular class such as benzene from toluene and methanol from ethanol (see also B. J. Doleman et al., Anal. Chem. 1998, 70, 4177–4190).

G. A. Sotzing et al., Chem. Mater., 2000, 12, 593–595, describe a polyaniline-carbon black chemiresistive detector which can be used to highly sensitive detect and discriminate biogenic amines. Electrically conductive polyaniline is used as the polymeric phase of a carbon black polyaniline composite. Sorption of an odorant into the polymeric phase of the composite produces a characteristic increase in the direct current electrical resistance response of the detector. The response of the detector is approximately six orders of magnitude greater to butylamine than to water, acetone, methanol, ethylacetate, and butanol.

S. D. Evans et al., J. Mater. Chem., 2000, 10, 183–188, use para-substituted thiophenol derivatives to stabilize gold nanoparticles. The nature of the substituent group is important for controlling the relative strength of the particle-particle and particle-solvent interactions and hence in determining the physical and chemical properties of these systems. Thin films of the particles were formed by solvent evaporation on microelectrode patterned surfaces. The films display ohmic behavior and the room temperature conductivities vary between $10^{-6}$ and $10^{-2}$ $\Omega^{-1}cm^{-1}$. Upon exposure to various chemical compounds, the thin films display a change in conductivity. The response to polar solvents display good repeatability, whereas the response to non-polar organic analytes tends to be less reproducible and displays a variety of time-dependent behavior. Depending upon the nature of the $\omega$-functional group different conductometric and elipsometric responses to the analytes in the vapor phase are displayed. The Au-nanoparticles are not interlinked through linker molecules.

A method for producing thin nanoparticle films with high accuracy is described in WO 96/07487. The film comprises Au-nanoparticles that are linked by bifunctional linker molecules. For assembling the thin film, first a substrate is treated with a bifunctional linker molecule, so that a first reactive group of the linker molecule reacts with the substrate, linking it thereto. When using, for example, a glass substrate, a mercaptoalkylsilane might be used as a linker molecule. The surface of the substrate is then covered with thiol groups. Next the substrate is dipped into a solution of Au-nanoparticles and the nanoparticles are attached to the thiol-groups on the surface of the substrate. The surface of the substrate is then covered with a layer of Au-nanoparticles. Afterwards the substrate is immersed in a solution of an alkyldithiol, which serves as a bifunctional linker molecule and binds with one thiol group to the surface of the Au-particles. By repeating the steps of immersion in a solution of Au-nanoparticles and immersion in a solution of the bifunctional linker molecule a thin-film can be formed through self-organization of the components. The linker molecule comprises a hydrocarbon skeleton, that can be a linear or branched aliphatic chain which may contain multiple bonds or other groups to modify the electronic properties of the linker molecule. In the experiments 1,9-nonanedithiol was used as a linker molecule. The use of those thin films as sensors, e.g. for the detection of oxidants, such as chlorine or ozone, is proposed.

H. Wohltjen and A. W. Snow, Anal. Chem., 1998, 70, 2856–2859, describe a colloidal metal-insulator-metal ensemble chemiresistor sensor based on a monolayer stabilized metal nanocluster transducer film. The thin transducer film is composed of 2 nm gold clusters encapsulated by octanethiol monolayers and is deposited on an interdigitated microelectrode by air-brush technique. Upon exposure to organic vapor, large responses are displayed which were reversible. The sensor is sensitive to non-polar compounds, e.g. toluene and tetrachloroethylene, whereas little response for 1-propanol and water is displayed.

The assembly of a sensor based on self-organization of nanoparticle-films is described in more detail in WO 99/27357. First a substrate is functionalized with a mercaptoalkylsilane to provide binding sites for the nanoparticles. The activated substrate is then immersed in a solution, that contains Au-nanoparticles, which are stabilized by a thin shell of alkylthiols. The thiol-groups on the surface of the substrate substitute some of the alkylthiol-ligands bound to the surface of the Au-nanoparticle, thereby attaching the nanoparticle to the surface of the substrate. By subsequently attaching alternating layers of Au-nanoparticles and linker-molecules a thin film is assembled. In the experimental part the use of 1,8-octanedithiol as a linker molecule is described. Linker molecules functionalized for selectively interacting with specific analytes are not described. To modify the sensitivity of the sensor it is suggested to introduce heterofunctionality to the ligand shell. The ligand molecule would then be bifunctional, one functional group to bind with the metal core surface and the other to provide an attractive interaction for sorption of the target species. It was shown, that the chemical selectivity of the sensor could be tuned by the use of differently functionalized nanoparticles. It was further shown, that the size of the nanoparticles and the thickness of the ligand shell is influencing the chemical sensitivity. The sensors which were prepared by self-assembly were found to be most sensitive to toluene, but less sensitive to polar analytes (propanol and water).

WO 00/00808 describes sensor arrays for detecting an analyte in a fluid. These arrays comprise a plurality of compositionally different sensors. The sensors comprise a conductive material embedded in a matrix of a non conductive material, e.g. an organic polymer. As a conductive material nanoparticles might be used, that are optionally stabilized by ligand molecules attached to the central core. The ligand molecules can also be polyhomofunctionalized or polyheterofunctionalized. As an insulating material preferably organic polymers are used. It is further suggested to use an alkylthiol ligand as the sole insulating matrix.

A further sensor is described in FR 2783051. The sensor comprises a nanoparticle film, in which the nanoparticles are stabilized by ligand molecules with at least one functional unit to bind to the nanoparticle surface and at least one functional unit to interact with an analyte molecule.

Although the results obtained with the above-described chemical sensors are encouraging, there still is a need for improvement of the selectivity towards the analytes detected as well as an improvement as towards the stability of the performance of the sensor, e.g. signal and base-line stability.

It therefore is an object of the invention to provide a chemical sensor with an enhanced selectivity towards analytes and a high stability in performance.

To solve this object, the present invention provides a chemical sensor, comprising a substrate, a nanoparticle film formed on the substrate, the nanoparticle film comprising a nanoparticle network formed of nanoparticles interlinked through linker molecules having at least two linker units capable of binding to the surface of the nanoparticles, and at least one selectivity-enhancing unit having a binding site for reversibly binding an analyte molecule, and detection means for detecting a change of a physical property of the nanoparticle film.

Nanoparticles are small particles of various shape, that have a maximum size in at least one direction between 0.4 nm and several 100 nm. There are known nanoparticles having about the same size in all three directions in space as well as nanowires, nano fibers, and nanotubes having a larger size in one direction in space, and nanosheets having a larger size in two directions in space. All those nanoparticles may be used in the assembly of the chemical sensor. The preparation of nanoparticles is described in numerous publications and is well-known to persons skilled in the art.

The nanoparticles are interlinked by linker molecules. These linker molecules comprise a molecule back-bone and are at least bifunctional, i.e. they comprise at least two linker units that bind to the surface of a nanoparticle. Binding can be achieved e.g. through covalent binding, complex formation, ionic interaction or dipole interaction. Binding must be strong enough to ensure formation of a nanoparticle network. The linker units bind to the surface of neighboring nanoparticles so that the nanoparticles are interlinked to form a nanoparticle network. Such interlinking of the nanoparticles improves the mechanical properties of the chemical sensor and thereby reduces problems with base-line drifts, signal fluctuations, and mechanical deterioration (for example when using the sensor in liquid media). Furthermore, linker molecules which are capable of interlinking nanoparticles enable the fabrication of reproducible and homogenous nanoparticle films via "layer-by-layer" assembly. Nanoparticle films assembled through layer-by-layer technique can be made very thin (ca. 5–500 nm) and with high precision. They provide a comparably high mechanical strength and do e.g. come not off when immersed into liquids. Because of their improved stability those sensors may not only be applied to gaseous analytes, but may also be used to detect analytes in liquids. The linker molecules may be bifunctional to interlink two nanoparticles, but also may be polyfunctional. Such a polyfunctional linker molecule is capable of attaching to the surface of a nanoparticle with several linker units, thereby strengthening the attachment of a linker molecule to the surface of the nanoparticle. Further, it is capable of interlinking more than two nanoparticles with each other and, thus, further increase the stability. The molecular structure of the linker molecule may also comprise branches which are not terminated by a linker unit.

To improve the selectivity of the nanoparticle film towards analytes, preferably polar analytes, the linker molecule comprises besides the linker units at least one selectivity-enhancing unit having a binding site for reversibly binding an analyte molecule. The selectivity-enhancing unit preferably forms part of the molecule back-bone or is a terminating unit of a branch. The molecule back-bone of the linker molecule may be best-defined as the structural part of the linker molecule which forms the longest connection between two interlinked nanoparticles.

Binding or coordination within the scope of the invention and when used for describing the interaction between the linker molecule and the analyte preferably means a reversible binding or coordination of the analyte molecule to the selectivity-enhancing unit. Preferably no covalent bonds are formed between the selectivity-enhancing unit and the analyte molecule. On the other hand binding must be strong enough to achieve a sufficient increase in selectivity. The analyte may form a covalent bond with the selectivity-enhancing unit. Then the chemical sensor can be used only once to detect the analyte, and thereby the sensitive film of the chemical sensor is irreversibly altered. Because of the broader applicability, a reversible binding of the analyte to the selectivity-enhancing unit is preferred.

Different types of interactions may occur between the analyte and the selectivity-enhancing unit. The selectivity-enhancing group may be charged or may be a dipolar unit, which may form hydrogen bonds, or may comprise a highly polarizable electron system. The interaction between the analyte and the selectivity-enhancing unit may be a coulombic interaction between two charged groups, between a charged group and a dipole or between two dipoles, or a polarization interaction between a charge and an induced dipole or a dipole and an induced dipole. Also induced dipole/induced dipole interactions can cause a sufficiently strong interaction between the target analyte and the selectivity-enhancing unit. However, with respect to induced dipole/induced dipole interactions and within the scope of this invention, only highly polarizable units which comprise a delocalized π-electron system are considered as possible selectivity-enhancing units. The polarizability of alkylene chains is rather weak and therefore possible interactions with a target analyte are not strong enough to cause a selectivity enhancement.

The structure and chemical nature of the selectivity-enhancing group depends on the structure and chemical nature of the analyte to be detected. If the target analyte is a cation or comprises a cationic unit, then the selectivity-enhancing unit preferably comprises at least one functional group, which is capable of charge/charge or charge/dipole interactions. Preferably the selectivity-enhancing unit comprises anionic units and/or dipolar units (functional groups). If the analyte is a metal ion, then units that can act as bi- or multidentate donor ligands are especially preferred. If the target analyte is an anion or comprises an anionic unit, then the selectivity-enhancing unit preferably comprises at least one cationic unit and/or a dipolar unit. It is also possible that the selectivity-enhancing unit comprises a metal cation, which is bound through at least one donor ligand to the linker molecule. Most preferred are bi- or multidentate (chelating) ligands for binding the metal ion. A selectivity-enhancing unit comprising a metal cation is not only useful for enhancing the interaction with anionic analytes. Chelated metal ions can strongly interact with gases like $H_2S$, $NH_3$, $CO$, $O_2$, $NO_x$, $SO_x$, and are therefore well suited for enhancing the selectivity of a sensor for such gases.

If the analyte is polar, i.e. comprises a permanent dipole moment, then the selectivity-enhancing unit preferably comprises at least one permanent dipole moment to enable dipole/dipole interactions, and/or one charged unit to enable dipole/charge interactions.

If the target analyte can act as a hydrogen donor for forming hydrogen bonds, then the selectivity-enhancing unit should preferably comprise at least one dipolar unit, which can act as hydrogen acceptor. If the target analyte can act as hydrogen acceptor for forming hydrogen bonds, then the selectivity-enhancing unit preferably comprises at least one unit, which can act as hydrogen donor.

If the target analyte is non-polar in nature but comprises a polarizable structural unit, e.g. a delocalized π-electron system, then the selectivity-enhancing unit should preferably also be non-polar in nature and should preferably comprise a polarizable delocalized π-electron system.

The mechanism by which a physical property of the nanoparticle film changes in the presence of an analyte is not yet fully understood. The inventors provide some theoretical considerations to explain the effect, but this should not be understood as limiting the scope of the invention. One possible explanation for the influence of an analyte on e.g. the conductivity of the nanoparticle film may be a change in the dipole moment of the linker molecule. By binding of the analyte molecule to the at least one selectivity-enhancing unit, an electronic interaction occurs which will change the dipole moment of the analyte and of the selectivity-enhancing unit. If the selectivity-enhancing unit is e.g. involved in the charge carrier transport (while driving a current through the film), a change of the dipole moment may strongly effect the transport properties of the sensor material and therefore change the resistance of the device. Therefore a preferred feature of the selectivity-enhancing unit is that its dipole moment changes upon interaction with analyte molecules.

Another possible mechanism to explain a change in e.g. the conductivity of the nanoparticle film is that the interactions between adjacent linker molecules are disturbed in the presence of an analyte. Adjacent linker molecules of the nanoparticle network may interact with one-another through the selectivity-enhancing unit and/or through other groups (e.g. a fine-tuning unit, see below). Such interaction can be through dipole-dipole interactions (including von der Waals interactions) and/or through hydrogen bonds. It has been shown in the literature that interactions through hydrogen bonds between organic molecules (forming a molecular monolayer on a substrate) can enhance the electronic coupling along molecular assemblies (s. Sek et al., J. Phys. Chem. B 2000, 104, 5399–5402). If now analyte molecules diffuse into the nanoparticle film and interact with the selectivity-enhancing unit (and other groups), the interaction between the linker molecules is disturbed and, thus, the electronic transport properties of the nanoparticle film are affected. This effect will contribute to the sensor signal when using the nanoparticle film, for example, in a chemiresistor setup.

The selectivity-enhancing group may further interact intramolecularly with other groups within the linker molecule. This may be through hydrogen bonds or dipole interactions. When an analyte is coordinated to the selectivity-enhancing unit these intramolecular interactions are disturbed, what also has an effect, e.g., on the electronic transport properties of the nanoparticle film.

The chemical sensor according to the invention may be used in various types of chemical sensor devices that use different physical properties to detect an analyte. In a first group, a change of an electrical property is detected. For example, a change in conductivity or capacity of the nanoparticle film may be measured. Therefore, the chemical sensor may act as a chemiresistor or a chemicapacitor. The nanoparticle film can also be utilized in a configuration forming a chemidiode or a multiterminal device, such as a chemitransistor (e.g. Chem-FET). The chemical sensor may also be used as a mass sensitive sensor. The nanoparticle film is then used as a coating on a piezo-electric material to form a chemically sensitive surface acoustic wave (SAW) device or a quartz crystal microbalance (QCM).

According to another embodiment, the chemical sensor is used as an optical sensor. The sensor signal may then be measured as a change in reflectance, fluorescence, absorption, or scattering. For example a charge transfer complex may be formed between the analyte and the selectivity-enhancing unit, what will lead to a change in the optical properties of the sensor. It is also possible to utilize the nanoparticle films as chemically sensitive coatings for fiber optics (e.g. optodes, interferometer devices).

The chemical sensor can also use changes in heat or temperature and therefore be used as a thermistor, or other thermoelectric device.

Preferably the chemical sensor is used as a chemiresistor.

The nanoparticle film may be deposited onto interdigitated electrodes, e.g. made of Au, which were deposited on an inert substrate, e.g. by lithographic techniques, or both electrodes may be deposited on top of the film. Also other configurations are possible. One electrode may be positioned below the nanoparticle film and the other may be deposited on top of the nanoparticle film. By the binding of the analyte to the selectivity-enhancing unit the electronic properties of the sensor are influenced resulting in a change of conductivity of the nanoparticle film.

The inert substrate can be made for example of $Si/SiO_2$ when the chemical sensor is integrated in an IC device. Further preferred substrates are made of glass and/or ceramics.

Several chemical sensors which preferably have different compositions of the nanoparticle film may be arranged to form a sensor array.

In a preferred embodiment the sensitivity enhancing unit may form a hydrogen bond to the analyte. The selectivity-enhancing unit then is a hydrogen donating or hydrogen accepting group.

The selectivity-enhancing group may be a charged unit. Examples for such charged units are metal cations of main group metals, transition metals and/or rare earth metals, cationic units and/or anionic units. The selectivity-enhancing unit may further be a dipolar unit having a permanent dipole moment. According to a further embodiment, the selectivity-enhancing unit is a polarizable structural unit. Examples for such polarizable structural units are aromatic π-electron systems, e.g. derived from benzene, naphthalene, azulene, fluorene, anthracene, phenanthrene, pyrene, chrysene, naphthacene, triphenylen, etc., or conjugated π-electron systems, e.g. —C=C—C=C— etc. Aromatic π-systems are preferred as a polarizable structural unit.

Preferably, the at least one selectivity-enhancing unit is selected from the group consisting of

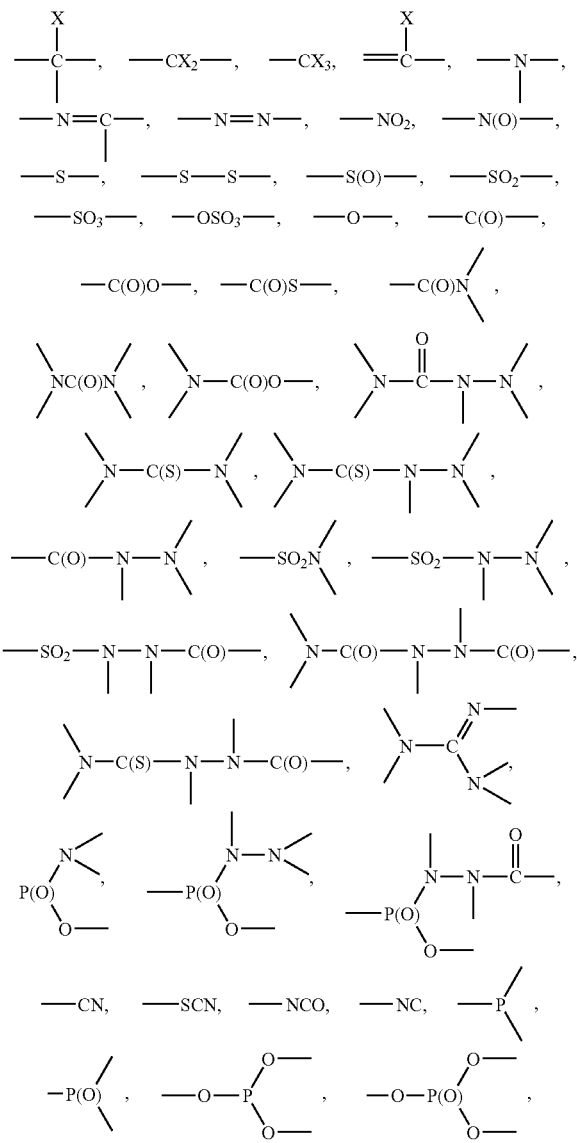

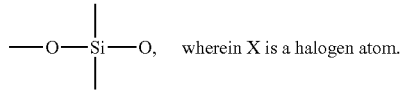

wherein X is a halogen atom.

Monovalent groups, e.g. —OH, —CN, etc. are preferably connected to the molecular back-bone or a branch of the linker molecule. Divalent groups, e.g. —S—, —S—S—, —O—, —N=N—, etc., may be integrated in the molecular back-bone or a branch or may be terminated on one end by e.g. a small alkyl group, preferably having 1 to 8 carbon atoms, an aryl group, preferably having 5 to 10 carbon atoms, or may carry a hydrogen atom. The selectivity-enhancing unit may also be protonated or deprotonated to form a cationic group, or to form an anionic group. The selectivity-enhancing group is then connected either directly or through a connecting unit e.g. an alkylene group, preferably having 1 to 8 carbon atoms, to the molecule back-bone of the linker group with its other valence. Selectivity-enhancing units having three or more valences may form a branch within the molecule back-bone or a branch of the linker molecule or some of the valences may carry an alkyl group, preferable having 1 to 8 carbon atoms, e.g. a methyl group, an aryl group having 5 to 10 carbon atoms, or may carry a hydrogen atom. These groups then are connected to the molecule back-bone as described above for the mono- and divalent groups.

Also combinations of the above mentioned groups are possible.

The selectivity-enhancing group may also form an integral part of a heterocyclic group. Such groups may be derived e.g. from pyridine, pyrimidine, pyrrole, pyrrolidine, furane, thiazole, etc.

Preferably, the at least one selectivity enhancing group is an amido group.

The linker units may be terminating groups in the linker molecule in order to stably interlink nanoparticles with each other. They may also be integrated into a molecule chain. In this case, binding to the nanoparticle may also give a dangling branch. It is noted that bi- or polyfunctional linker molecules may comprise either terminating linker units or linker units which are integrated into a molecule chain. Also any combination of both types of linker units is possible.

To obtain a sensor, that can be used over a longer period of time without deterioration of its properties, the nanoparticle network has to provide a sufficient stability. Preferably, the linker unit is a terminating group which allows a better binding of the linker unit to the surface of a metal nanoparticle.

In order to establish a stable nanoparticle network, the linker unit of the linker molecule has to bind to the surface of the nanoparticle. Preferred linker units are selected from the group consisting of

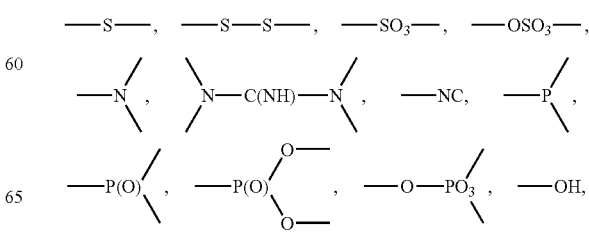

-continued

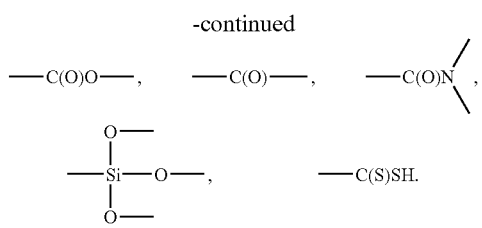

The above-mentioned functional groups may form a terminating group. Then the valences not bound to the linker molecule may carry a hydrogen atom or a small alkyl group, preferably comprising 1 to 8 carbon atoms, e.g. a methyl group or may be deprotonated to form an ionic unit. The linker group may also be integrated in e.g. an alkylene chain.

The linker units within a linker molecule may be the same or different.

To further enhance the selectivity, the linker molecule preferably comprises at least one fine-tuning unit arranged in the vicinity of the selectivity-enhancing unit, in such a way that the fine-tuning unit is capable of interacting with the analyte molecule bound to the selectivity-enhancing unit. The interaction between the analyte molecule and the fine-tuning unit may be sterically, electronically, or through hydrogen bonding. By the interaction between the analyte molecule and the fine-tuning unit, the interaction between the selectivity-enhancing unit and the analyte molecule can be modulated, i.e. enhanced or reduced.

The interactions between the analyte and the fine-tuning unit may be the same as mentioned above for the selectivity-enhancing unit. Therefore the fine-tuning unit may comprise the same functional or structural units as mentioned above for the selectivity-enhancing unit. The fine-tuning unit and the selectivity-enhancing unit within a linker molecule therefore may be same or different. The interactions between the analyte and the fine-tuning unit must effect a reversible bonding of the analyte. Therefore also non-covalent bonding occurs between the analyte and the fine-tuning unit. The bonding towards the fine-tuning unit does not have to be as strong as for the selectivity-enhancing group. Therefore also weak interactions, like van der Waals forces occurring between alkyl groups, can be used to modulate the selectivity of the sensor. In such cases, the fine-tuning unit may also be an alkyl group, preferably having 1 to 10 carbon atoms, wherein the alkyl group may be linear or branched and may carry further substituents.

The modulating effect can also be achieved by introducing steric hindrance and thereby spatially preventing or reducing the attractive interactions between the selectivity-enhancing unit and the analyte. Thus, if only very small analytes should be allowed to interact with the selectivity-enhancing unit, the fine-tuning unit will comprise a spatially demanding unit, e.g. a branched alkyl group, a benzyl or a substituted benzyl group, which is positioned in close vicinity to the selectivity-enhancing unit. If however the steric hindrance does not need to be so severe (e.g. the size-exclusion effect is intended to be just moderate) it is either possible to reduce the size of the fine-tuning unit or to increase the distance between the fine-tuning unit and the selectivity-enhancing unit.

The fine-tuning unit preferably forms a secondary interaction site of the linker molecule for interacting with the analyte. The main site of interaction between the analyte and the linker molecule takes places at the selectivity-enhancing unit. However, in the vicinity the fine-tuning unit is available as another functional or structural unit that modulates the interaction with the analyte. Thus, the linker molecule has to be designed in a way which enables the concerted interaction of the analyte with the primary site of interaction (selectivity-enhancing unit) and the secondary site of interaction (fine-tuning unit). Depending on the intended effect of the chemical selectivity, the substituent must have suitable electronic or sterical properties. If, for example, a modulation of the chemical selectivity by sterical interaction is desired, then a spacious group, e.g. an alkyl residue which may be branched, is arranged in the vicinity of the primary interaction site. If additional electronic interactions are desired, the fine-tuning unit may be at least one functional group that may form a hydrogen bond or may be a halogen atom. If the fine-tuning unit has the proper configuration, it may be possible to achieve chiral selectivity by introducing a chiral group as a fine-tuning unit.

A huge structural diversity is possible for the fine-tuning unit and the structure is depending on the analyte to be detected. Polar groups as mentioned above for the selectivity-enhancing unit may be chosen to establish an interaction of the analyte and the fine-tuning unit by hydrogen bonds or dipole-dipole interaction. Further highly polarizable π-electron systems may be used, e.g. aromatic systems comprising several phenyl rings, that also may be condensed to form more extended π-electron systems. Also conjugated π-electron systems might be used, comprising several double or triple bonds, to form a polarizable unit, that can non-covalently interact with an analyte having a large permanent dipole momentum or that may be charged. Also weakly polarizable groups may be used. Examples are linear or branched alkyl or cycloalkyl groups, preferably having 1 to 20 or 5 to 20 Carbon atoms, respectively. These groups are preferred as sterically demanding groups shielding the selectivity-enhancing unit from larger molecules.

For modulating the selectivity of the linker molecule towards target analyte molecules, it is sufficient that the molecular structure of the linker molecules brings the primary (selectivity-enhancing unit) and secondary (fine-tuning unit) interaction sites close enough together so that concerted interaction with the analyte molecule is possible. Of course, it is also possible that more than one primary and/or secondary site of interaction may be arranged in the same linker molecule. They may interact either with the same or several different analyte molecules.

For establishing a close spatial relationship between the selectivity-enhancing unit and the fine-tuning unit, the linker molecule preferably comprises a directing unit, connecting the selectivity-enhancing unit and the fine-tuning unit in a way, that the fine-tuning unit is positioned in the vicinity of the selectivity-enhancing unit, such that an analyte bound to the selectivity-enhancing unit may interact with the fine-tuning unit.

The directing unit has to spatially arrange the selectivity-enhancing unit and the fine-tuning unit to allow the fine-tuning unit to modulate the interaction between the selectivity-enhancing unit and the analyte. Preferably, the directing unit is a hydrocarbon skeleton, which may be saturated or may be (partly) non-saturated. More preferably, the directing unit is a rather rigid moiety comprising at least one cyclic unit (e.g. derived from cyclohexene, cyclopentane, etc.) or, even more preferable, an aromatic unit (e.g. derived from benzene, naphthalene, azulene, fluorene, anthracene, phenanthrene, pyrene, chrysene, naphthacene, triphenylene, etc.). Those cyclic units may also comprise heteroatoms, such as O, S, and N atoms (e.g. the directing unit may be derived from thiophene, benzothiophene, dibenzothiophene, thianthrene, furan, pyran-2H, pyran-4H, isobenzofuran, benzofuran, pyrrole, imidazole, pyrazole, pyridine, pyrazine, pyrimidine, pyridazine, indazole, indole, isoindole, indolizine, phtalazine, chinoline, purine, chinolizine-4H, phenazine, acridine, carbazole, oxazole, isoxazole, piperidine, pierazine). The heteroatoms may also act as selectivity-enhancing unit and/or fine-tuning unit.

For constructing an appropriate directing unit, a combination of a broad variety of structural elements is possible. In the simplest case the directing unit is just a covalent bond connecting the selectivity-enhancing unit and the fine-tuning unit with one another. The directing unit may be an alkylene group having 1 to 10 carbon atoms, wherein at least one $CH_2$ group may be substituted by an ethenyl group and/or ethynyl group, and further at least two ethenyl and/or ethynyl groups may constitute a conjugated bond system, and/or a cycloalkylene group having 5 to 10 carbon atoms, and/or an aromatic group having 6 to 18 carbon atoms, wherein several phenyl rings may be condensed, and further the aromatic group may comprise at least one heteroatom, preferably an N, O, S, or Si atom, and in said groups at least one hydrogen atom may be substituted by an alkyl group having 1 to 6 carbon atoms which may be linear or branched.

The linker units, the selectivity-enhancing unit(s) and the fine-tuning unit(s) may be connected through connecting units. The connecting units may be formed of alkylene, alkenylen and/or alkynylen groups.

Preferably the linker molecule comprises a delocalized π-electron system, e.g. formed of conjugated double bonds and/or aromatic groups. Nanoparticle films comprising those linker molecules have a better conductivity and therefore can be made thinner. This decreases the length of diffusion paths within the film and allows the assembly of sensors, which are very sensitive and show a fast response.

The linker molecules used for the assembly of the chemical sensor are made up of different units, wherein every unit is chosen according to the analytical problem to be solved. The skilled person therefore can tailor the chemical sensor towards the target analyte. This can e.g. be done by molecular modeling methods.

It is obvious to the skilled person, that a partition of the linker molecules into several different units serves as a model to develop a structure of a linker molecule tailored to an analyte. In practice some overlapping occurs in the functions of the units. For example a part of the directing unit may also act as a fine-tuning unit or as a selectivity-enhancing unit and vice versa.

The linker molecules should not be too large to ensure the formation of homogenous films by the layer-by-layer technique and to enable a precise control over the film thickness. Preferably the linker molecules have a molecular weight of 100 to 2000 g/mol, especially preferred 100 to 1000 g/mol, most preferred 100–600 g/mol.

In a preferred embodiment, the chemical sensor comprises a linker molecule, in which the directing unit is a ring system comprising 4 to 18 carbon atoms which may be aromatic or non-aromatic and in which up to four carbon atoms of the ring system may be sustituted by a heteroatom, independently selected from the group consisting of O, N, S, the at least one selectivity-enhancing unit is an amido group and/or an ester group attached to the ring system through the carbonyl carbon atom, the nitrogen atom, or the oxygen atom, and the at least one fine-tuning group is a substituent of the ring system, selected from the group consisting of a hydrogen atom, a halogen atom, an alkyl group having 1 to 6 carbon atoms, an amine group, a hydroxy group, and a carbonyl oxygen atom.

The non-aromatic ring system of the directing unit may be derived from cyclohexane or cyclopentane and the aromatic ring system of the directing unit may be derived from benzene, naphthalene, azulene, fluorene, anthracene, phenanthrene, pyrene, chrysene, naphthacene, or triphenylene.

In an even more preferred embodiment, the chemical sensor comprises a linker molecule, in which the selectivity-enhancing unit is an amido group, the directing group is a phenylene ring and/or a cyclohexylene ring and the fine-tuning unit is a hydrogen atom, a halogen atom, a hydroxy group, an amino group, an alkoxy group having 1 to 6 carbon atoms, and/or an alkyl group having 1 to 6 carbon atoms. The linker molecule may further comprise thiol groups as linker units, which bind to the surface of a nanoparticle. The linker units may be connected to the selectivity-enhancing unit by an alkylene group having 1 to 6 carbon atoms.

In a preferred embodiment, the linker molecule comprises at least one amino acid or amino acid derivative. Preferably, the linker molecule comprises at least two amino acids or amino acid derivatives which are the same or different, and which preferably are linked to each other through amide bonds.

Linker molecules with selectivity-enhancing properties can conveniently be assembled by utilizing amino acids as molecular building blocks. One advantage of using α-amino acids to prepare the linker molecules is that many different amino acids are readily available. Moreover, to synthesize the linker molecules, it is possible to use well-elaborated protocols which were originally developed for peptide synthesis. A linker molecule may comprise one or more amino acid structure which may have the same or different residues. If more than one amino acid is used to form the linker molecule, they may be interlinked through amide (peptide) bonds. The combination of different amino acid structures enables one to create a broad variety of different linker molecules having distinct chemical selectivities. Preferably the number of amino acid acid structure comprised in one linker molecule is $\leq 10$, more preferably $\leq 5$. Most preferably the following α-amino acids are used: glycine (Gly), alanine (Ala), valine (Val), leucine (Leu), isoleucine (Ile), methionine (Met), proline (Pro), phenylalanine (Phe), tryptophan (Trp), serine (Ser), threonine (Thr), cystelne (Cys), tyrosine (Tyr), asparagine (Asn), glutamine (Gln), aspartic acid (Asp), glutamic acid (Glu), lysine (Lys), arginine (Art), histidine (His). These amino acids can also be derivatized for further tuning the interaction with the analyte. For example, functional groups may be left protected after synthesizing the linker molecules. Besides, α-amino acids, β-, γ-, . . . ω-amino acids, or the corresponding D-isomers can be used in principle as well as the L-isomers.

The selectivity of the nanoparticle film may be further modulated when the linker molecule comprises at least one cage compound, cyclodextrine, crown ether, cryptate, porphyrine, phthalocyanine and/or cyclam. The linker molecules may further contain azobenzene, rotaxanes, and/or biphenyl groups.

In still another preferred embodiment, the linker molecule comprises a metal and/or a metal cation.

The nanoparticles which may be made from metals, semiconductors, or insulators fulfill two different tasks. First, they strongly determine the physical properties of the composite film material which are measured when operating the sensor. If the sensing principle requires electric conductivity, then metal particles are preferred because they strongly enhance the electric conductivity of the material.

This allows, for example, measuring changes of the electric conductivity as the sensor signal. As a rule of thumb, the use of larger particles leads to films with higher conductivity than using smaller ones. Moreover, many metal and semiconductor nanoparticles have pronounced optical properties (absorption and luminescence) which may change upon interaction of the analyte with the film material. Second, the nanoparticles serve as nanoscopic substrates for binding the bi- or polyfunctional linker molecules. In this sense, the nanoparticles can be considered as junctions of the nanoparticle/linker network. These nanoparticle networks comprise cavities in-between the nanoparticles which support the diffusion of analyte species into the film material.

For the use of the nanoparticle film as a chemiresistor, an important function of the nanoparticles is to provide sufficient conductivity. Therefore, the nanoparticle preferably is a metal nanoparticle. Metals suited for the fabrication of a nanoparticle film are preferably selected from the group consisting of Au, Ag, Pt, Pd, Cu, Ni, Cr, Mo, Zr, Nb, Fe. It is also possible to use combinations (e.g. alloys) of these metals for preparing the nanoparticles. It is also possible to use semiconductor nanoparticles (e.g. II/VI semiconductors such as CdS, CdSe, CdTe, ZnO, ZnS, ZnSe, ZnTe, HgS, HgSe, HgTe, or III/V semiconductors such as GaAs, InP, or others such as PbS, $Cd_3P_2$, $TiO_2$ and other transition metal oxides, or combinations of these materials, e.g. core/shell structures). In order to enhance the conductivity of the semiconductor nanoparticles, they may be doped (e.g. As, Sb, Al, B, P, In, lanthanides, transition metals). Further, also combinations of metals, semiconductors, and/or insulators may be used as nanoparticles. In principle, it is also possible to provide conducting or semiconducting nanoparticles from conducting organic materials such as conducting polymers. It is understood that the nanoparticles mentioned here can also be used in any combination for preparing the sensitive materials.

Preferably the chemical sensor is formed as a chemiresistor, wherein the nanoparticle film is deposited on a pair of contacting electrodes or vice versa. The electrical resistance of the nanoparticle film is altered by the presence of an analyte. Other sensor systems in which the above-described nanoparticle film can be used are e.g. optical chemical sensors. In this case, the binding of analyte molecules to the linker molecules leads to a change of optical properties (UV/vis and/or IR). Suitable materials may comprise, for example, semiconductor nanoparticles which show electro- and or photo-luminescence. The luminescence properties may change when the analyte molecules bind to the linker molecules. The linker molecules electronically couple to the nanoparticle's electronic structure. When the analyte-linker molecule interaction induces a change in the electronic structure (energy levels) of the linker molecules, this influences the electronic structure of the nanoparticles. Therefore the optical properties of the nanoparticle material change. Examples of suitable semiconductor materials are already given above.

The nanoparticle film may be formed by a one-step procedure described by Leibowitz et al. Anal. Chem. 199, 71, 5076–5083. However, to obtain stable nanoparticle films with high precision, the nanoparticle film is preferably prepared through layer-by-layer deposition of the nanoparticles. The assembly of the nanoparticle film occurs through self-organization of the nanoparticles and of the linker molecules. This allows a formation of the nanoparticle film under controlled and reproducible conditions. A further subject of the invention therefore is a method for forming a chemical sensor as described above, comprising the following steps:

a) functionalization of a substrate to provide linking units on the surface of the substrate;
b) deposition of a layer of nanoparticles on the functionalized substrate surface;
c) deposition of bi- or polyfunctional linker molecules on the layer of nanoparticles and coupling of the bi- or polyfunctional linker molecules to the nanoparticles;
d) deposition of a further layer of nanoparticles and linking them through the bi- or polyfunctional linker molecules with the nanoparticles of the first layer;
e) repeating steps c) and d) until a homogenous film of nanoparticles is obtained.

The deposition of the nanoparticles and the deposition of the bi- or polyfunctional linker molecules is repeated until a nanoparticle film is obtained which has sufficient conductivity for being used as a chemiresistor (preferably R<1 MOhm). The deposition of the nanoparticles and of the bi- or polyfunctional linker molecules may be performed by any suitable method. The nanoparticles or the bi- or polyfunctional linker molecules may be deposited by spraying or dipping with a solution of the nanoparticles or of the bi- or polyfunctional linker molecules in a suitable solvent and evaporation of the solvent or by a spin-coating technique. Usually the nanoparticles are applied in the form of a solution of ligand-stabilized nanoparticles. Binding of ligand or linker molecules is achieved via ligand-exchange reactions. In such exchange reactions, at least some of the stabilizing ligands are exchanged by the linker molecules. For example, dodecylamine ligands on the surface of Au-nanoparticles are easily exchanged by thiol functionalized linker molecules.

The chemical sensor according to the invention may be miniaturized, e.g. to be used in a sensor array in an IC device. The chemical sensor comprises at least one nanoparticle and at least two linker molecules or at least two nanoparticles and at least one linker molecule.

The chemical sensor may comprise a single nanoparticle to which two linker molecules are attached. The linker molecules may then be attached e.g. to electrodes with their respective other ends.

According to another embodiment, the chemical sensor may comprise a single linker molecule which is attached to two nanoparticles.

The above-described sensor may be used for the detection of analyte molecules. A further subject of the invention therefore is a method for detecting an analyte, wherein the nanoparticle film of a chemical sensor as described above is exposed to the analyte and a change of a physical property of the nanoparticle film is measured by a detection means. The change of a physical property may be e.g. a change in conductivity, dielectric constant, reflectance, luminescence, absorbence, mass, volume, density, and/or heat capacity.

The invention will now be described in more detail by way of examples and with reference to the accompanying figures.

FIGS. 1a–c show schematically the generalized structures of linker molecules;

FIGS. 2a–d show a model for the interaction between the analyte and the selectivity-enhancing unit and some possible structural arrangements of the selectivity-enhancing unit, the directing unit, and the fine-tuning unit within the linker molecule;

FIG. 3a–n show schematically the general principle for designing linker molecule, and linker molecules designed according to these principles;

FIG. 4a–c show arrangements of an analyte interacting with a linker molecule;

Figure 4:
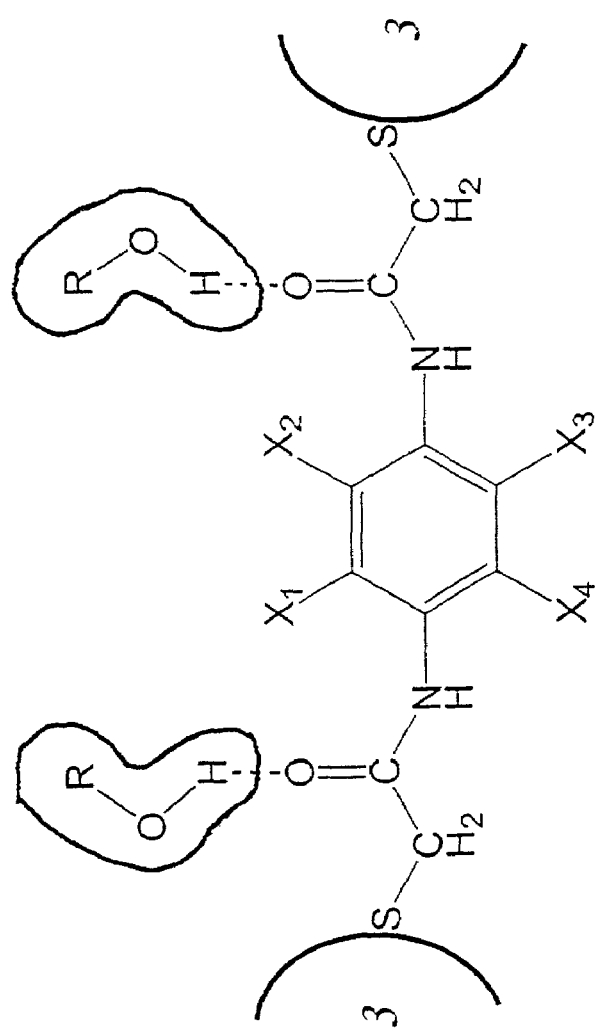

FIG. 7a–b show the response traces of sensors during repeated exposure to dry air or solvent vapor;

FIG. 8 shows an assembled chemiresistor.

FIG. 1 shows the generalized structure of the linker molecules which form a nanoparticle network by interlinking nanoparticles. The units which enable the selective interaction with the analyte have been omitted in these generalized structures. However, it is understood that each structure comprises at least one selectivity-enhancing unit. These units can be positioned anywhere along the molecular structure (back-bone, junctions, and/or branches). In FIG. 1a, the simplest structure of the linker molecule is shown. The linker molecule comprises a molecule back-bone 1 which is terminated by linker units 2. The linker units 2 bind to the surface of nanoparticles 3, thereby interlinking the nanoparticles 3 and forming a nanoparticle network. In FIG. 1a, the linker molecule is bifunctional. However, not only bifunctional, but also polyfunctional linker molecules allow interlinking of nanoparticles. Such a polyfunctional linker molecule is shown in FIG. 1b. The molecule back-bone 1 forms branches 4 which are terminated by linker units 2. Such a polyfunctional linker molecule is capable of interlinking more than two nanoparticles 3. The linker units must not be a terminating group, but may also be integrated into a molecule chain. In this case, the branch of the molecule back-bone 1 is not terminated by a linker unit 2 and forms a dangling branch 5 (FIG. 1c). Furthermore, not every branch has to be terminated by a linker unit 2, these branches also form dangling branches 6 which do not bind the nanoparticle (FIG. 1c).

FIG. 2 shows a section of the molecule back-bone 1 of a linker molecule to explain different possibilities of the arrangement of selectivity-enhancing unit 8, analyte 7, and fine-tuning unit 9.

In FIG. 2a, the linker molecule back-bone 1 comprises only a selectivity-enhancing unit 8, to which an analyte 7 is bound. In FIGS. 2b to 2d, an additional fine-tuning unit 9 is present which forms a secondary interaction site for the analyte 7 and thereby modulates the interaction between the analyte 7 and the selectivity-enhancing unit 8. The selectivity-enhancing unit 8 and the fine-tuning unit 9 are connected through the directing unit 13. There are different possibilities for the arrangement of the selectivity-enhancing unit 8 and the fine-tuning unit 9 within the linker molecule. The fine-tuning unit 9 may form the terminating end of a branch of the molecule back-bone 1 (FIG. 2b). Further it is possible that the fine-tuning unit 9 is integrated in the molecule back-bone 1 (FIG. 2c). As a third possibility, the fine-tuning unit 9 may be integrated in a branch 11 of the molecule back-bone 1.

FIG. 3a shows schematically the simplest possible structure of a linker molecule fulfilling the basic criteria of the present invention. It comprises two linker units 2 for interlinking two nanoparticles and one selectivity-enhancing unit 8 for selective interaction with a target analyte. The two linker units are terminating functional groups which are connected with the selectivity-enhancing unit 8 through connecting units 19. FIG. 3b gives a specific example of a linker molecule complying with the scheme of FIG. 3a. The linking units 2 are thiol groups which can bind to many metal (e.g. Au, Ag, Pt) or semiconductor (e.g. CdSe, CdTd) nanoparticles. The selectivity-enhancing unit 8 is a secondary amine group which introduces a permanent dipole moment into the molecular structure. Moreover, the amine group can act as a hydrogen bond base. Therefore, this selectivity-enhancing unit tunes the selectivity of the sensor towards polar analyte molecules, especially to those which are capable of acting as a hydrogen bond acid. The connecting units 19 which link the amine group 8 to the thiol groups 2 are formed by —$CH_2$—$CH_2$— fragments.

FIG. 3c schematically shows another simple structure of a linker molecule comprising one selectivity-enhancing unit 8. However, in contrast to FIG. 3a, the selectivity-enhancing unit 8 does not form an integral part of the molecule back-bone 1. Instead, it is attached to the molecule back-bone 1. An example of this arrangement is given in FIG. 3d. In this case, the selectivity-enhancing unit 8 is formed by a hydroxyl group which tunes the selectivity towards polar analytes capable of forming hydrogen bonds. However, in contrast, in FIG. 3b the hydroxyl group does not have the basicity of an amine group. The molecule back-bone 1 is formed by a pentylene chain which is terminated at both ends by a thiol group 2 as linking units.

FIG. 3e schematically shows a linker molecule having two selectivity-enhancing units 8 integrated into the molecule back-bone 1. The linking units 2 are attached on both sides through connecting units 19. FIG. 3f shows a specific example of such structural arrangement. The molecule back-bone 1 is formed of a butylene unit (—$(CH_2)_4$—) which is connected at both ends to the nitrogen atoms of an amido group serving as the selectivity-enhancing units 8. These selectivity-enhancing units 8 have a dipole moment and easily form hydrogen bonds. Therefore, the selectivity of the sensor is tuned towards polar hydrophilic substances. The carbonyl carbon atoms are connected to the linking units 2 through methylene groups (—$CH_2$—) acting as connecting units 19.

FIG. 3g shows schematically an extension of the foregoing structure: a fine-tuning unit 9 is inserted in-between the two selectivity-enhancing units 8. The selectivity-enhancing units 8 are connected with the fine-tuning unit 9 through a directing unit 13. FIG. 3h shows a specific molecular structure complying with the scheme of FIG. 3g. In this case, the fine-tuning unit 9 is a nitrogen atom which is integrated into the directing unit 13. The fine-tuning unit (=N—) has a pretty strong basicity and introduces an additional dipole moment. Therefore, it fine-tunes the selectivity towards polar, acidic, or ionic analytes. The fine-tuning unit and the directing unit form a 2,6-substituted pyridine ring. The substituents which form the selectivity-enhancing units 8 are two amido groups. They are connected with the pyridine ring through the carbonyl carbon atoms. The directing unit 13 keeps the fine-tuning unit 9 in close vicinity to the selectivity-enhancing units 8. This allows, for example, multidentate binding of a metal cation. The linking units 2 are connected through —$CH_2$—$CH_2$— fragments 19 with the amido nitrogen atoms.

FIG. 3i schematically shows a more complex linker molecule in which four fine-tuning units 9 are connected to the central directing unit 13. FIG. 3j shows a specific arrangement of this structural arrangement. In this case, the directing unit 13 is a substituted benzene ring which brings the selectivity-enhancing units 8 and the fine-tuning units 9 into close vicinity. At 1,4-positions, the ring system is connected with two amido groups as selectivity-enhancing units 8 through the nitrogen atoms. At 2,3- and 5,6-positions are substituents $X_1$–$X_4$ forming the fine-tuning units 9 which can be, for example, hydrogen atoms, alkyl residues, halogen atoms, or functional groups such as —$NH_2$, —OH, etc. If, for example, the alkyl group is a spatially demanding substituent (e.g. a branched alkyl residue), then the approach of an analyte molecule to the selectivity-enhancing units is sterically hindered. This tunes the selectivity towards small analyte species which are sterically less hindered. In addition, a functional group such as an amino group or a hydroxy group further enhances the formation of hydrogen bonds between the linker molecule and a suitable analyte molecule.

FIG. 3$k$ schematically shows the structure of a linker molecule comprising four selectivity-enhancing units 8 which are formed by chemically different groups (8.1 and 8.2). The molecule also comprises a directing unit 13 and a fine-tuning unit 9. As shown by the example of FIG. 3$l$, this structure can conveniently be assembled by using two amino acids as building blocks. More specifically, the central part of the structure comprises one isoleucine (Ile) unit and one arginine (Arg) unit which are connected with each other by formation of an amido group (peptide bond) which forms the central selectivity-enhancing unit 8.1. The carboxylic acid group of arginine has been converted into an additional amide group (forming another selectivity-enhancing unit 8.1) which connects the molecule to the linking unit 2 (a thiol group) through a $CH_2$—$CH_2$— fragment 19.1. The amine group of isoleucine has also been used to attach another —$CH_2$—$CH_2$— fragment 19.1 via an additional amide group (additional selectivity-enhancing unit 8.1) to the linker molecule. This end of the molecule is also terminated by a thiol group as the second linking unit 2. The α-carbon atom of isoleucine forms the directing unit 13 to which a branched alkyl residue is attached forming the fine-tuning unit 9 of the molecule. This fine-tuning unit introduces steric hindrance and therefore modulates the interaction of the analyte molecules with the selectivity-enhancing units 8. The residue of arginine comprises a guanidine group as an additional selectivity-enhancing unit 8.2 which is a very strong organic base. This group is easily protonated to form a cationic moiety. The selectivity is therefore tuned towards anions or analyte molecules comprising anionic moieties or polar acidic analytes capable of forming hydrogen bonds. The guanidine group is attached to the linker molecule via a —$(CH_2)_3$— fragment and the a-carbon atom of arginine forming the connecting unit 19.2.

FIG. 3$m$ schematically shows a symmetric linker molecule comprising four linking units 2 and six selectivity-enhancing units 8. FIG. 3$n$ shows an example of a linker molecule complying with this structural arrangement. The structure of a crown ether (18-crown-6) forms the central part of the molecule. The six ether (—O—) units 8 are well arranged for interacting with metal ions, especially potassium. The ethylene groups 19.1 connect the ether oxygen atom with one another. The crown ether skeleton is substituted by four methylene units (19.2) which connect the structure to thiol groups as linking units 2. Related to the example of a cyclic polyether are other molecular structural units which can also be utilized for binding metal cations (e.g. —COO—; —(NH—$CH_2$—$CH_2$—NH)—; —(N═CH—CH═N)—; —(S—$CH_2$—$CH_2$—$CH_2$—S)—, —(N═CH—CH═N—CH═CH—N)═, —$N(CH_2COO^-)_2$, crown ethers, cryptates, porphyrins, phtalocyanines. Metal cations which are connected to the linker molecule can serve themselves as selectivity-enhancing units for gases, such as $H_2S$, $NH_3$, CO, $O_2$, $NO_x$, $SO_x$.

In the examples of FIG. 3, the linker units 2 are thiol units. However, the function of the linker units is to attach the linker molecule to at least two nanoparticles and, thus, interlinking them. Therefore, each linker molecule comprises at least two linker units which may be the same functional units or may be different from each other. Examples of the linker units are: —SR, —SSR, —$SO_3R$, —$OSO_3R$, —$NR_2$, —NHC(NH)—$NH_2$, —NC, —$PR_2$, —$P(O)R_2$; —$PO_3R_2$, —$OPO_3R_2$, —OH, —COOR, —C(O)H, $C(O)NR_2$, —$Si(OR)_3$, —C(S)SH, and the ionic forms of these functional units (Where R is H or an organic residue which can be a terminating or a non-terminating residue. If R is a non-terminating residue, it can be a connecting unit, a part of the molecule back-bone, or a branch of the molecular structure which can be connected to other functional or structural units. If the functional or structural unit is directly bound to another functional or structural unit, then R stands for that other functional or structural unit.).

The examples of FIG. 3 also show some possible functional units and structural units which can act as selectivity-enhancing unit 8. However, it is understood that many other functional and structural units can be utilized which can serve to enhance the attractive (but non-covalent) interactions between the linker molecule and analytes of a selected compound class. Tab. 1 gives examples for units which are charged, which are dipolar units, which can form hydrogen bonds, or which are strongly polarizable. It may be necessary to combine these units with small connecting units (e.g. —$CR_2$—, ═CR—, etc.) in order to connect them with each other, or to connect them to (or to integrate them into) the linker molecule, as have been shown in principle by the examples given above. Of course, they may also be connected directly to each other. If a metal cation is part of the selectivity-enhancing unit, the ion is coupled to the linker molecule through at least one donor ligand. It is noted that some of the functional units given in Tab. 1 may be integrated into a cyclic and possibly aromatic structural unit (e.g. —S—, —O—, —NR—, ═N—).

Tab. 1 Examples of different functional and structural units supporting different types of interactions (R is H or an organic residue which can be a terminating or a non-terminating residue. If R is a non-terminating residue, it can be a connecting unit, a part of the molecule back-bone, or a branch of the molecular structure which can be connected to other functional or structural units. If the functional or structural unit is directly bound to another functional or structural unit, then R stands for that other functional or structural unit. X is a halogen atom).

I) Charged units
    metal cations
        main group metals (e.g. $Mg^{2+}$, $Ca^{2+}$, $Pb^{2+}$, etc.)
        transition metals (e.g. $Mn^{2+}$, $Co^{2+}$, $Fe^{2+/3+}$, $Cu^{2+}$, $Ag^+$, $Zn^{2+}$, $Cd^{2+}$, $Hg^{2+}$, $Cr^{3+}$, etc.)
    rare earth metals (e.g. $Ce^{3+}$, $Eu^{3+}$, etc.)
    cationic units (e.g. —$NR_3^+$, —$(NR_2)^+$—, —$NHC(NH_2)_2^+$)
    anionic units (e.g. —$S^-$, —$O^-$, —$C(O)O^-$, —$SO_3^-$, —$OSO_3^-$, —$PO_3^{2-}$, —$OPO_3^{2-}$, —$(OPOO^-)$, —$O(PO_2)O_3^{2-}$), —$C_5H_4^-$
II) Dipolar units (permanent dipole moment), incl. hydrogen bond donors and acceptors, e.g. —$CR_2X$, —$CRX_2$, —$CX_3$, ═CRX, —$NR_2$, —(NR)—, —(N═CR)—, —$NO_2$, —SR, —($CR_2$—S)—, ═(CR—S)—, —SO)—, —($SO_2$)—, —$O(SO_2)O$—, —$SO_3R$, —OR, —($CR_2$—O)—, ═(CR—O)—, —(C(O))—, —C(O)R, —C(O)OR, —$C(O)NR_2$, —(C(O)NR)—, —(NRC(O)NR)—, —(NRC(O)NRNR)—, —(NRC(S)NR)—, —(NRC(S)NRNR)—, (C(O)NRNR)—, —($SO_2NR$)—, —($SO_2NRNR$)—, —($SO_2NRNRC(O)$)—, —(NRC(O)NRNRC(O))—, —(NRC(S)NRNRC(O))—, —NRC(NR)(NR_2), —($PO_3NR$)—, —($PO_3NRNR$)—, —(PO₃NRNRCO)—, —(C(O)O)—, —CN, —NCO, —NC, —PR₂, —(PR)—, —(POR₂), —(POR)—, —OPO(OR)₂, —(OPOORO)—, —(OSiR₂O)—, etc.)

III) Polarizable structural units (aromatic π-electron system. e.g. —C₆R₃, —(C₆R₄)—; conjugated π-electron systems, e.g. —C═C—C═C—, etc.)

The examples given in FIG. 3 also show same possible functional and structural units which can serve as fine-tuning units. However, the general function of the fine tuning unit 9 is to modulate the interaction between the selectivity-enhancing unit 8 and the analyte. This can be achieved by introducing additional interactions (coulombic interactions involving charges and permanent dipoles, and/or polarization interactions) between the analyte and the linker molecule. The fine-tuning unit therefore may comprise the same functional or structural units as the selectivity-enhancing unit listed in Tab. 1. Addionally, the modulating effect can also be achieved by introducing steric hindrance. This may be achieved by introducing sterically demanding organic residues which may be saturated hydrocarbon groups or non-saturated hydrocarbon groups which may constitute an aromatic structural unit, e.g. a benzyl group.

FIG. 3 also gives examples for directing units 13. The function of the directing unit is to connect the selectivity-enhancing unit 8 and the fine-tuning unit 9 with each other. Preferably, the directing unit has to spatially arrange the selectivity-enhancing unit and fine-tuning unit to allow the fine-tuning unit to modulate the interaction between the selectivity enhancing unit and the analyte. Preferably, the directing unit is a hydrocarbon skeleton which may be saturated or may be (partly) non-saturated. More preferably, the directing unit is a rather rigid moiety comprising at least one cyclic unit (e.g. derived from cyclohexane, cyclopentane, etc.), or even more preferably an aromatic unit (e.g. derived from benzene, naphthalene, azulene, fluorene, antbracene, pheanthrene, pyrene, chrysene, naphthacene, triphenylene, etc.). The directing unit may also comprise heteroatoms, such as O, S, and N atoms. These heteroatoms can then function as the fine-tuning unit, as shown by the example of FIG. 3g (e.g. the directing unit may be derived from thiophene, benzothiophene, dibenzothiophene, thianthrene, furan, pyran-2H, pyran-4H, isobenzofuran, benzofuran, pyrrole, imidazole, pyrazole, pyridine, pyrazine, pyrimidine, pyridazine, indazole, indole, isoindole, indolizine, phthalazine, chinoline, purine, chinolizine-4H, phenazine, acridine, carbazole, oxazole, isoxazole, iperidine, piperazine). However, in the simplest case the directing unit is just a covalent bond connecting the selectivity-enhancing unit and the fine-tuning unit with one another.

It is noted that the fine-tuning unit may not necessarily need to be directed to the close vicinity of the selectivity-enhancing unit in order to fine-tune the chemical selectivity of the nanoparticle film although such arrangement is preferred. The fine-tuning unit can also tune the overall chemical nature of the nanoparticle film. If, for example, the fine-tuning units comprise non-polar hydrophobic residues (e.g. alkyl or aryl residues), then the film will become more hydrophobic. Therefore, the selectivity is tuned towards hydrophobic analytes. If, instead, the fine-tuning group comprises polar functional units, then the film will become more hydrophilic and, thus, the selectivity is fine-tuned towards hydrophilic analytes.

By combining the above-mentioned structural units, a linker molecule can be designed for each analytical problem or analyte to be detected.

FIG. 4 shows the structure of a linker molecule which can be used to obtain a nanoparticle network. The molecule corresponds to the one shown in FIG. 3j. The linker molecule comprises a directing unit that is formed by a phenylene ring which may be substituted by substituents $X_1$, $X_2$, $X_3$, $X_4$. Bound to the phenylene ring are two amido groups which form the selectivity-enhancing units (primary interaction groups). The linker units of the linker molecule are formed by thiol groups which are linked to the amido groups via a methylene group as a connecting unit. The thiol groups acting as thiolate linker groups bind to the surfaces of nanoparticles 3.

FIG. 4a shows the formation of hydrogen bonds between a hydroxylic analyte and the carbonyl group of the amide functionalized linker molecule. If spatial hindrance does not prevent the approach of the hydroxy oxygen atom to the amide bond, the amide proton may also be involved in hydrogen bonding, as shown in FIG. 4b.

As long as spatial hindrance is not too severe, also a polar aprotic analyte (e.g. acetone) can interact through the amide proton with the linker molecule (FIG. 4c).

Figure 5:
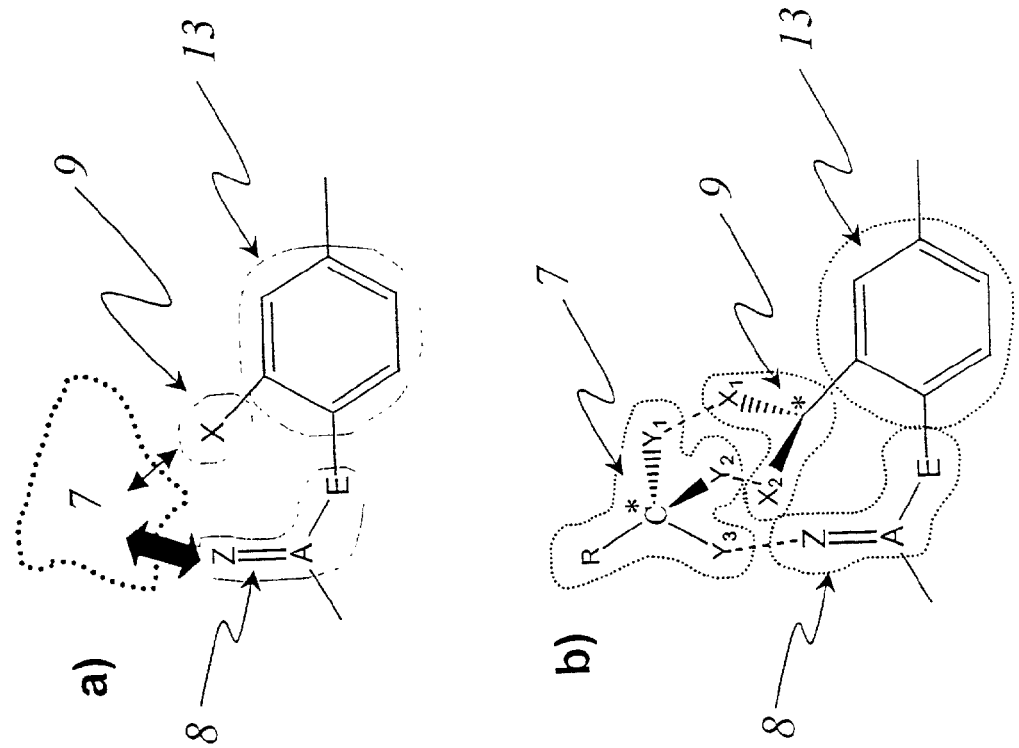
FIG. 5 shows a model for explaining the interaction between a linker molecule and an analyte via benzene substitution.

The interaction with the fine-tuning unit (secondary interaction site) is shown in more detail in FIG. 5. The substituent X of the benzene ring which forms the fine-tuning unit is located in the vicinity of the analyte molecule which is bound to the atom Z (e.g. carbonyl-O of an amido group) of the selectivity-enhancing unit (primary interaction site). In case the modulating group X is an alkyl group, a sterical interaction to the analyte molecule occurs which may weaken the interaction of the analyte molecule with the primary binding site Z. In case X is an hydroxy or an amino group, hydrogen bonds may be formed to the analyte molecule so that the analyte molecule is bonded more firmly to the linker molecule. If the modulating substituent has the proper configuration, it may be possible to achieve chiral selectivity as shown in FIG. 6b. Instead of using a benzene ring, it is also possible to use other structural units in order to bring the substituent X in the vicinity of the primary interaction site. It is, for example, possible to utilize a cyclohexane ring linked to the primary interaction site. Similar as the benzene ring, the cyclohexane ring may be substituted with modulating groups X.

For testing the chemical selectivity of the chemical sensors, several linker molecules were synthesized. The structure of the molecules is shown in Scheme 1.

Scheme 1
structures of linker molecules used for sensor fabrication.

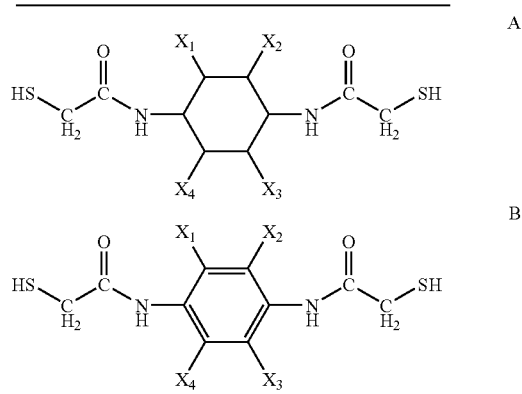

These molecules have two thiol groups which can bind to the surface of nanoparticles. Furthermore, each linker molecule comprises two amide bonds (—C(O)NH—) which enable the enhanced chemical selectivity for polar analytes. The central part of the molecules is either a cyclohexylene ring or a phenylene ring (molecules A and B. respectively). These central parts have substituents $X_1$ to $X_4$ which fine-tune the interaction between the analyte molecules and the linker molecules and, thus, the chemical selectivity of the chemical sensor. Table 2 shows the different substituents that have been used to modify the linker molecules A and B and gives abbreviations which will be used furtheron.

TABLE 2

Substituents of molecules A and B given in Scheme 1

| Molecule | X1 | X2 | X3 | X4 | Abbreviation |
|---|---|---|---|---|---|
| A | H | H | H | H | DMAA-CH |
| B | Cl | H | Cl | H | DMAA-DCB |
| B | H | H | H | H | DMAA-B |
| B | $CH_3$ | H | $CH_3$ | H | DMAA-DMB |

DMAA-CH: 1,4-Di-(mercaptoacetamido)-cyclohexane
DMAA-DEB: 1,4-Di-(mercaptoacetamido)-2,5-dichloro-benzene
DMAA-B: 1,4-Di-(mercaptoacetamido)-benzene
DMAA-DMB: 1,4-Di-(mercaptoacetamido)-2,5-dimethyl-benzene As a comparison, 1,9-nonandithiol (NDT) has been used as bifunctional linker molecules which did not comprise a selectivity-enhancing unit. Furthermore, sensors have been fabricated by depositing dodecylthiol (DT) stabilized Au-nanoparticle via spin-coating onto interdigitated electrode structures.

The nanoparticles and the chemiresistor devices have been obtained according to the following general procedures.

1. Preparation of Metal Nanoparticles a) Dodecylamine Stabilized Au-Nanoparticles:

These docecylamine stabilized Au-nanoparticles are prepared similar as described recently in Ref.: D. V. Leff, L. Brandt, J. R. Heath, Langmuir, 1996, 12, 4723.

To a rapidly stirred solution of 160 mg $AuCl_3$ in 20 ml water, a solution of 639 mg tetraoctylammoniumbromide in 20 ml toluene were added. It was stirred until the organic phase turned into orange, while the aqueous phase turned colorless. To the mixture 1178 mg dodecylamine and 10 ml toluene were added, turning the organic phase from orange to red. Under vigorous stirring, a freshly prepared solution of 221 mg $NaBH_4$ in 15 ml water was added. The color of the solution immediately turned to deep purple. After stirring over night under ambient conditions, the organic phase was separated and 80 ml ethanol were added. The mixture was stored in a freezer at −18° C. over night. By filtration through a nylon membrane (0.45 µm pore size) the precipitate was separated from the solution and redissolved in 17.5 ml toluene. This solution was subjected to fractionated precipitations which were done by repeating the following three steps:
1. addition of ethanol (5 to 20 ml);
2. letting sit over night in a freezer;
3. separation of the precipitate by centrifugation.

This way, four fractions were obtained and used for sensor fabrication. TEM analysis revealed that the Au-nanoparticles were crystalline and had diameters between 2 and 20 nm.

b) Dodecylthiole Stabilized Au-nanoparticles

These nanoparticles were prepared similar as described by Brust and Coworkers (J. Chem. Soc., Chem. Commun. 1994, 801–802). To a rapidly stirred solution of 206 mg $AuCl_3$ in 20 ml water, a solution of 840 mg tetraoctylammoniumbromide in 20 ml toluene were added. It was stirred until the organic phase turned orange, while the aqueous phase turned colorless. To the mixture 33 µl dodecylthiol in 20 ml toluene were added, turning the organic phase from orange to red. Under vigorous stirring, a freshly prepared solution of 257 mg $NaBH_4$ in 20 ml water was added. The color of the solution immediately turned black. After stirring over night under ambient conditions, the organic phase was separated and 40 ml ethanol were added. The mixture was stored in a freezer at −33° C. for 7 hours. By filtration through a nylon membrane (0.45 µm pore size), the precipitate was separated and redissolved in a few ml toluene giving the first fraction. To the filtrate, 40 ml ethanol were added and the mixture was stored in the freezer over night. After separating the second fraction, 40 ml ethanol were added and a third fraction was separated after storing in the freezer over night. The fractionated precipitation was continued several times giving six fractions of dodecylthiol stabilized Au-nanoparticles. TEM analysis of the third fraction revealed that the diameter of the metal core of the nanoparticles was around 3 to 6 nm.

Fabrication of Chemiresistor Sensor Devices a) Substrate Cleaning and Amino Functionalization:

The metal nanoparticle films were deposited onto BK7-glass substrates, each having three lithographically made interdigitated electrode structures. The electrode structures comprised a 5 nm titanium adhesion layer on which a 95 nm gold layer was deposited. They comprised 50 finger pairs having a width of 10 µm, a spacing of 10 µm, and an overlap of 1800 µm. Before assembling the nanoparticles onto the substrates, they were cleaned with acetone and isopropanol before applying an oxygen plasma (plasma conditions: approx. 4 min at 30 W and 0.5 mbar). The cleaned substrates were immersed into a solution of 50 µl 3-aminopropyldimethylethoxysilane in 5 ml toluene and heated to 60° C. for 30 minutes. This procedure functionalized the glass substrates with amino groups which served as linking units for subsequent nanoparticle deposition.

b) Sensor Fabrication Via Layer-by-layer Deposition of Au-Nanoparticles:

After washing the substrates with toluene, they were immersed for 5 minutes into a toluene solution containing dodecylamine stabilized Au-nanoparticles. Next, the substrates were rinsed with solvents and then immersed into the linker solution. When using the amide functionalized linker molecules listed in Tab. 2, the substrates were washed with toluene and DMF and then immersed into a solution of 1 to 5 mg linker compound in 5 ml DMF. When using the 1,9-nonanedithiol linker, 2-propanol could be used instead of DMF. In this case, approximately 160 µl linker were dissolved in 4 ml 2-propanol for preparing the linker solution. After keeping the substrates for 5 minutes in the linker solution, they were rinsed with DMF (or 2-propanol) and toluene. Then, the procedure of immersing the substrates into nanoparticle solution and linker solution was repeated until the deposited films had a sufficiently low resistance (typically in the kΩ to MΩ regime, measured through the interdigitated electrode structures).

c) Sensor Fabrication Via Spin-coating:

A drop of a solution of dodecylthiol stabilized Au-nanoparticles was placed onto the electrode structures of an amino functionalized substrate. After a few seconds, the substrate was spun to produce a film of non-interlinked Au-nanoparticles.

Testing the Chemical Selectivity of the Chemiresistor

For investigating the sensor characteristics, the sensor chips were mounted in a test cell made from Teflon®. The sensors were connected to the measurement equipment through gold-plated pogo pins pressing onto the contact pads of the electrode structures. Usually, the sensors were operated by applying a constant direct current (using a Keithley source-measure unit 236) and measuring the change of voltage across the electrodes (using a Keithley 2002 multimeter) while applying a test gas atmosphere. The current for each sensor was adjusted in a range between 0.3 to 150 µA so that the resulting voltage across the sensor electrodes was around 0.1 V. Thus, the power consumption was in the range between 0.03 to 15 µW.

Vapors of the solvents were generated with commercial gas calibration systems (Kalibriersystem MK15/MK5 or MK15/DDS-RL/MK5, Umwelttechnik MCZ GmbH, Obermörlen, Germany). These systems comprise bubblers and condensers for preparing saturated solvent vapors in a temperature range between 15 to 50° C. By using several mass flow controllers, the saturated vapors were diluted with zero-gas to a concentration in the range of 0.5 to 6000 $ppm_v$. As zero-gas purified and dried air (dew point −70° C.) was used which was provided by a commercial zero-gas generator (Nullgasanlage MD2000-25, Umwelttechnik MCZ). The mass flow system was equipped with a computer controlled valve for switching the gas flow through the sensor cell between zero-gas and test-gas. As test-gas vapors were used toluene, 1-propanol, and acetone. The actual concentrations of the vapors in the test cell were calculated by using the Antoine equitation and the dilution factors adjusted by the mass flow system. The mass flow in the test chamber was adjusted to 2 l/min and kept constant for all experiments.

Figure 6:
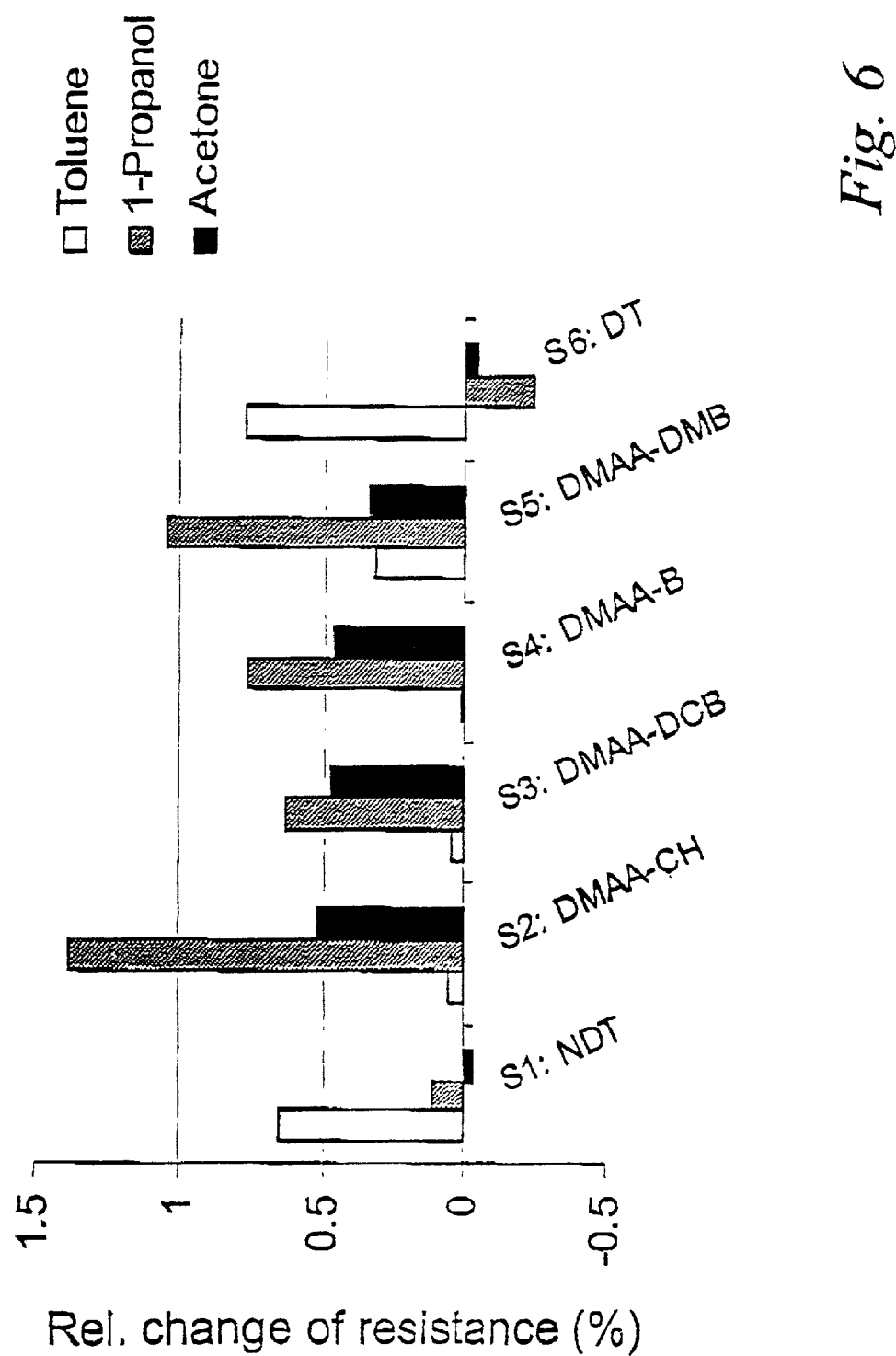
FIG. 6 shows the sensor response to different solvent vapors.

Table 3 and FIG. 6 summarize the experimental results obtained by exposing the sensors to three different solvent vapors at a concentration of 2400 $ppm_v$.

Figure 7:
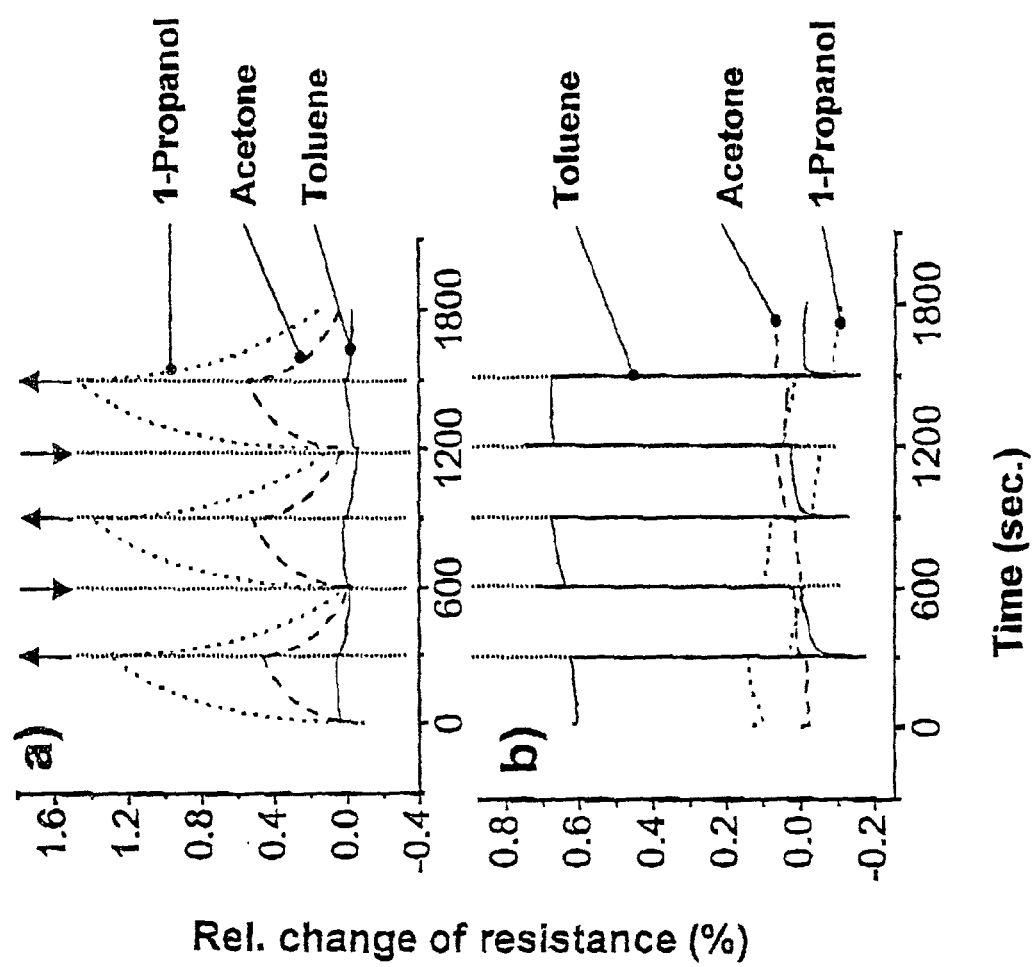

The amido functionalization of the linker molecules strongly influences the sensor dynamics. FIG. 7a shows typical response traces of a sensor made with an amide functionalized linker molecule (e.g. DMAA-CH) (In FIG. 7 an arrow up means injection of air and an arrow down means injection of vapor). It is seen that even after 5 minutes exposure to 1-propanol vapor the sensor signal was still rising. For comparison, FIG. 7b shows the response curve of sensor S1 made with 1,9-nonanedithiol. The sensor responded much faster and reached a stable signal after a few seconds. Also sensor S6 which did not contain amide functionalized linker molecules responded similarly fast as sensor S1. The rather slow response observed for the amide functionalized sensors may be explained by structural changes accompanying the interaction of polar analyte molecules with the amide group. Since the amido-functionalized linkers are pretty rigid molecules, structural changes are much more hindered and should not be as fast as conformational changes of alkylene chains which may accompany adsorption of analyte molecules to sensors S1 and S6.

Finally, the results summarized in Tab. 3 and FIG. 6 suggest that the chemical selectivity of the chemiresistors could be fine-tuned by varying the molecular structure in the vicinity of the amide functions. Thus, using either a cyclohexyl or a benzene ring as the central part of the molecule and/or varying the substituents $X_1$ to $X_3$ clearly changed the signal ratios of each sensor (S2 to S5).

TABLE 3

Relative changes of resistance after exposing the sensors to solvent vapors at 2400 $ppm_v$ for 300 seconds. The abbreviations for the linker molecules used to prepare the sensors are given in the head of each column. If necessary, the results were corrected for baseline drifts.

| Solvent vapor @ 2400 $ppm_v$ | S1 NDT | S2 DMAA-CH | S3 DMAA-DCB | S4 DMAA-B | S5 DMAA-DMB | S6 DT |
|---|---|---|---|---|---|---|
| Toluene | +0.65%[1] | +0.06%[2] | +0.52% | +0.01% | +0.32%[3] | +0.77%[1] |
| 1-Propanol | +0.11%[1] | +1.38%[2] | +0.63%[2] | +0.76%[2] | +1.04%[3] | −0.24%[3] |
| Acetone | −0.03%[1] | +0.52%[2] | +0.47%[2] | +0.46%[2] | +0.34%[3] | −0.04%[1] |

[1]Signals reached a stable value
[2]Signal was still increasing
[3]Signal was close to reach a stable value Toluene was used as a typical non-polar solvent. 1-propanol was chosen as a typical hydroxylic solvent, whereas acetone served as a typical polar aprotic solvent. It is readily seen in FIG. 6 that sensor S1 which was made with 1,9-nonanedithiol (NDT) had a pronounced selectivity for the non-polar toluene vapor. This was expected, because the linker molecules used did not comprise any polar functional groups (besides the two thiol groups which bind the nanoparticles). Also sensor S6 which was made with dodecylthiol (DT) stabilized Au-nanoparticles showed selectivity towards toluene vapor. The non-polar character of the dodecyl residues surrounding the particles also explains this result. The results obtained with this sensor are in agreement with results reported previously by Wohltjon and Snow (loc. cit.). In strong contrast, sensors S2 to S4 which were made with the amide functionalized linker molecules showed pronounced selectivity for the polar solvent acetone and, especially, the hydroxylic solvent 1-propanol. Also sensor S5 was selective towards 1-propanol, however, the response to the non-polar solvent toluene and the aprotic solvent acetone were similar. The same selectivity patterns as represented by FIG. 6 were qualitatively observed over the whole concentration range of 60 to 2400 $ppm_v$.

FIG. 8 shows a chemiresistor which has a nanoparticle film as a sensitive element. On a glass substrate 15 are placed interdigitated electrodes 16. On the substrate is deposited a nanoparticle film 17, which covers the electrode structures 16. A current may be applied to the leads 18 of the electrodes and a change in the current may be detected by a detector (not shown). The detailed part of the figure shows the nanoparticles 3 interlinked through linker molecules 12 thereby forming a nanoparticle network.

The invention claimed is:
1. Chemical sensor, comprising
a substrate,
a nanoparticle film formed on the substrate, the nanoparticle film comprising
a nanoparticle network formed of nanoparticles interlinked through linker molecules having at least two linker units capable of binding to the surface of the nanoparticles, and
at least one selectivity-enhancing unit having a binding site for reversibly binding an analyte molecule, and
detection means for detecting a change of a physical property of the nanoparticle film, wherein the linker molecule comprises at least one fine-tuning unit arranged in the vicinity of the selectivity-enhancing unit in such a way, that the fine-tuning unit is capable of interacting with the analyte molecule bound to the selectivity-enhancing unit.

2. Chemical sensor according to claim 1, wherein the selectivity-enhancing unit is capable of reversibly binding the analyte molecule.

3. Chemical sensor according to claim 1, wherein the binding site of the selectivity-enhancing unit is capable to bind the analyte through coulomb-ic interaction and/or through polarization interaction.

4. Chemical sensor according to claim 1, wherein the binding site of the selectivity-enhancing unit is a hydrogen bond donating group or a hydrogen bond accepting group capable of forming hydrogen bonding to the analyte.

5. Chemical sensor according to claim 1, wherein the at least one selectivity-enhancing unit is selected from the group consisting of

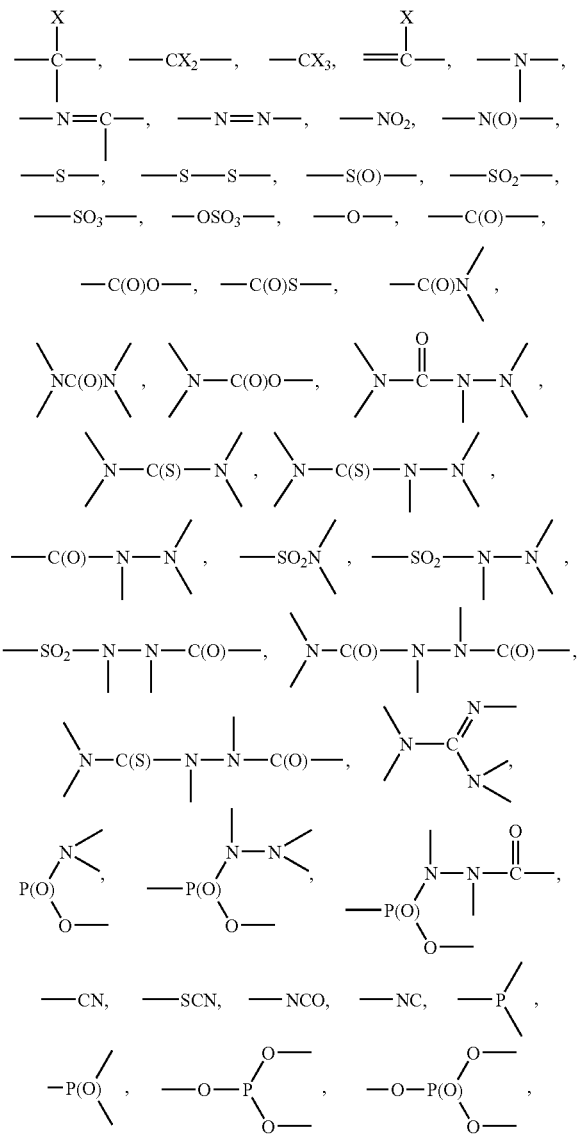

-continued

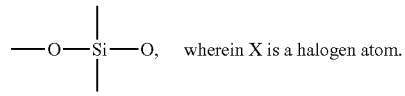

wherein X is a halogen atom.

6. Chemical sensor according to claim 1 wherein the at least one selectivity-enhancing unit is an amido-group.

7. Chemical sensor according to claim 1, wherein the linker unit is a terminating group.

8. Chemical sensor according to claim 1, wherein the linker unit is selected from the group consisting of

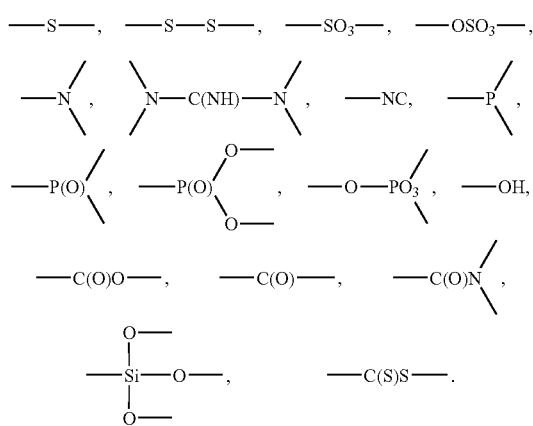

9. Chemical sensor according to claim 1 wherein the linker molecule comprises at least one directing unit, connecting the selectivity-enhancing unit and the fine-tuning unit in a way, that the fine-tuning unit is positioned in the vicinity of the selectivity-enhancing unit, such that an analyte bound to the selectivity-enhancing unit interacts with the fine-tuning unit.

10. Chemical sensor according to claim 9, wherein the directing unit is a bond, an alkylene group having 1 to 10 carbon atoms, wherein at least one $CH_2$ group may be substituted by an ethenyl group and/or ethynyl group, and further at least two ethenyl and/or ethynyl groups may constitute a conjugated bond system, and/or a cycloalkylene group having 5 to 10 carbon atoms, and/or an aromatic group having 6 to 18 carbon atoms, wherein several phenyl ring may be condensed, and further the aromatic group may comprise at least one heteroatom, preferably an N, O, S, or Si atom, and in said groups at least one hydrogen atom may be substituted by an alkyl group having 1 to 6 carbon atoms which may be linear or branched.

11. Chemical sensor according to claim 1, wherein the at least one selectivity-enhancing unit is an amido group, the at least one fine-tuning unit is a hydrogen atom, a halogen atom, an alkyl group having 1 to 6 carbon atoms, a hydroxy group, an amine group, and/or an alkoxy group having 1 to 6 carbon atoms, and the connecting unit is a phenylene group and/or a cyclohexylene group.

12. Chemical sensor according to claim 1, wherein the linker molecule comprises at least one amino acid or amino acid derivative.

13. Chemical sensor according to claim 1, wherein the linker molecule comprises at least one compound selected from the group consisting of cage compounds, cyclodextrins, crown ethers, cryptates, porphyrins, phthalocyanines, cyclams.

14. Chemical sensor according to claim 1, wherein the linker molecule comprises a metal and/or a metal cation.

15. Chemical sensor according to claim 1, wherein the nanoparticle is a metal nanoparticle.

16. Chemical sensor according to claim 15, wherein the metal nanoparticle comprises
a metal selected from the group consisting of Au, Ag, Pt, Pd, Cu, Ni, Cr, Mo, Zr, Nb, Fe, or any combination of those metals.

17. Chemical sensor according to claim 1, wherein the nanoparticle is a semiconductor nanoparticle.

18. Chemical sensor according to claim 17, wherein the seminconductor nanoparticle comprises
a II/IV semiconductor or a III/V semiconductor.

19. Chemical sensor according to claim 1, wherein the nanoparticle is an insulator nanoparticle.

20. Chemical sensor according to claim 1, wherein the sensor comprises at least one nanoparticle and at least two linker molecules, or at least two nanoparticles and at least one linker molecule.

* * * * *